US011304994B2

(12) United States Patent
Hsu et al.

(10) Patent No.: US 11,304,994 B2
(45) Date of Patent: Apr. 19, 2022

(54) RECOMBINANT INTRAVENOUS IMMUNOGLOBULIN (RIVIG) COMPOSITIONS AND METHODS FOR THEIR PRODUCTION AND USE

(71) Applicant: AB Biosciences, Inc., Concord, MA (US)

(72) Inventors: Yen-Ming Hsu, Lexington, MA (US); Jeng-Shin Lee, Lincoln, MA (US); Hsiu-Ching Chang, Concord, MA (US)

(73) Assignee: AB Biosciences, Inc., Concord, MA (US)

( * ) Notice: Subject to any disclaimer, the term of this patent is extended or adjusted under 35 U.S.C. 154(b) by 488 days.

(21) Appl. No.: 16/089,042

(22) PCT Filed: Mar. 29, 2017

(86) PCT No.: PCT/US2017/024650
§ 371 (c)(1),
(2) Date: Sep. 27, 2018

(87) PCT Pub. No.: WO2017/172583
PCT Pub. Date: Oct. 5, 2017

(65) Prior Publication Data
US 2019/0111115 A1 Apr. 18, 2019

Related U.S. Application Data

(60) Provisional application No. 62/315,483, filed on Mar. 30, 2016.

(51) Int. Cl.
| | |
|---|---|
| A61K 38/47 | (2006.01) |
| C07K 14/705 | (2006.01) |
| C07K 14/78 | (2006.01) |
| C07K 16/00 | (2006.01) |
| A61P 37/06 | (2006.01) |
| A61K 9/00 | (2006.01) |
| C07K 14/47 | (2006.01) |
| C07K 14/735 | (2006.01) |
| C12N 15/62 | (2006.01) |
| A61K 39/00 | (2006.01) |

(52) U.S. Cl.
CPC ............ *A61K 38/47* (2013.01); *A61K 9/0019* (2013.01); *A61P 37/06* (2018.01); *C07K 14/47* (2013.01); *C07K 14/70535* (2013.01); *C07K 14/70575* (2013.01); *C07K 14/70578* (2013.01); *C07K 14/78* (2013.01); *C07K 16/00* (2013.01); *C12N 15/62* (2013.01); *A61K 2039/505* (2013.01); *C07K 2317/52* (2013.01); *C07K 2319/30* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 7,279,329 | B2 | 10/2007 | Chou et al. |
| 7,410,953 | B2 | 8/2008 | Kawasaki |
| 8,669,350 | B2 | 3/2014 | Chou et al. |
| 9,683,044 | B2 | 6/2017 | Block et al. |
| 9,926,362 | B2 | 3/2018 | Strome et al. |
| 2009/0252729 | A1 | 10/2009 | Farrington et al. |
| 2009/0304696 | A1 | 12/2009 | Lawson et al. |
| 2013/0156765 | A1 | 6/2013 | Block et al. |
| 2014/0294817 | A1 | 10/2014 | Mosser et al. |
| 2014/0302026 | A1 | 10/2014 | Lee et al. |
| 2015/0004129 | A1 | 1/2015 | Tschopp et al. |

(Continued)

FOREIGN PATENT DOCUMENTS

| | | |
|---|---|---|
| CN | 104718223 A | 6/2015 |
| WO | 0200893 | 1/2002 |

(Continued)

OTHER PUBLICATIONS

Fan, C-Y, et al., "Production of multivalent protein binders using a self-trimerizing collagen-like peptide scaffold" The FASB Journal, 2008, vol. 22, pp. 3795-3804.
Jain, A., et al. "Tumour antigen targeted monoclonal antibodies incorporating a novel multimerisation domain significantly enhance antibody dependent cellular cytotoxicity against colon cancer," European Journal of Cancer (2013) 49, pp. 3344-3352.
Müller, K.M., et al., "The first constant domain (CH1 and CL) of an antibody used as heterodimerization domain for bispecific miniantibodies," FEBS Letters 422 (1998) pp. 259-264.
Nagashima, H., et al., "Tandemly repeated Fc domain augments binding avidities of antibodies for Fc—y receptors, resulting in enhanced antibody-dependent cellular cytotoxicity," ScienceDirect, Molecular Immunology 45 (2008) pp. 2752-2763.

(Continued)

*Primary Examiner* — Nora M Rooney
(74) *Attorney, Agent, or Firm* — Cesari & McKenna, LLP

(57) ABSTRACT

Compositions of recombinant intravenous immunoglobulin (rIVIG) proteins and methods for purification and use of rIVIG proteins. The compositions comprise oligomeric Fc molecules which bind to Fc receptors with high avidity. The rIVIG proteins are useful as immunomodulatory molecules for the treatment of immune disorders including autoimmune diseases, such as refractory immune thrombocytopenia, chronic inflammatory demyelinating polyneuropathy, multiple sclerosis, lupus, Graves Disease, Kawasaki disease, dermatomyositis, myasthenia gravis, Guillain-Barre syndrome, autoimmune hemolytic anemia, and other immune and inflammatory conditions. The rIVIG proteins can also be used as immunomodulators in patients to reduce the immune rejection of organ transplants, stem cell transplants and bone marrow transplantation. Additionally, the present invention provides rIVIG proteins of non-human origin, for use in veterinary immune disorders, such as canine rIVIG proteins for the treatment of dogs suffering from autoimmune hemolytic anemia, immune thrombocytopenia purpura, rheumatoid arthritis, or other canine immune disorder.

20 Claims, 6 Drawing Sheets

Specification includes a Sequence Listing.

(56) References Cited

U.S. PATENT DOCUMENTS

| | | |
|---|---|---|
| 2015/0038682 A1 | 2/2015 | Tsurushita et al. |
| 2015/0056185 A1 | 2/2015 | Strome et al. |
| 2015/0174237 A1 | 6/2015 | Mond et al. |
| 2015/0218236 A1 | 8/2015 | Pleass |
| 2016/0194395 A1 | 7/2016 | Amason et al. |
| 2017/0029505 A1 | 2/2017 | Griffin et al. |

FOREIGN PATENT DOCUMENTS

| | | | | |
|---|---|---|---|---|
| WO | 2008143954 | | 11/2008 | |
| WO | WO 2008/143954 | * | 11/2008 | ............ C07K 14/43 |
| WO | 2008151088 | | 12/2008 | |
| WO | WO-2008151088 A2 | | 12/2008 | |
| WO | 2012016073 | | 2/2012 | |
| WO | 2014031646 | | 2/2014 | |
| WO | WO-2014031646 A2 | | 2/2014 | |
| WO | 2015/158867 A1 | | 10/2015 | |
| WO | 2017024114 | | 2/2017 | |

OTHER PUBLICATIONS

Zuercher, A.W., et al., "Next-generation Fc receptor-targeting biologies for autoimmune diseases," Autoimmunity Reviews 18 (2019) 9 pages.

Patrick H.C. Van Berkel, et al. Rapid Production of Recombinant Human IgG With Improved ADCC Effector Function in a Transient Expression System. Biotechnology and Bioengineering. Feb. 1, 2010. 350-357. vol. 105, No. 2. Wiley Periodicals, Inc. The Netherlands.

* cited by examiner

FIGURE 1. CONSTRUCTS OF rIVIG MOLECULES
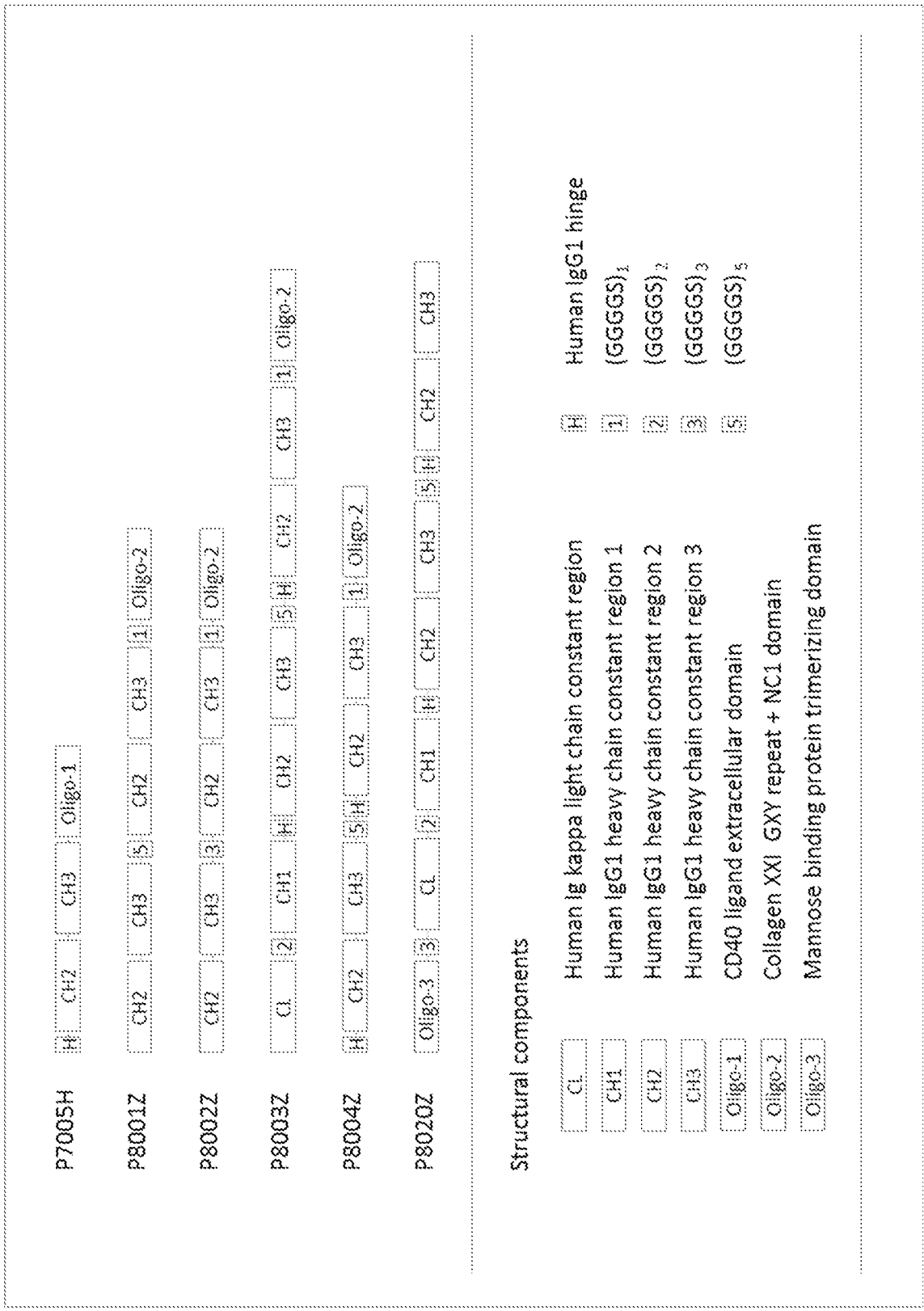

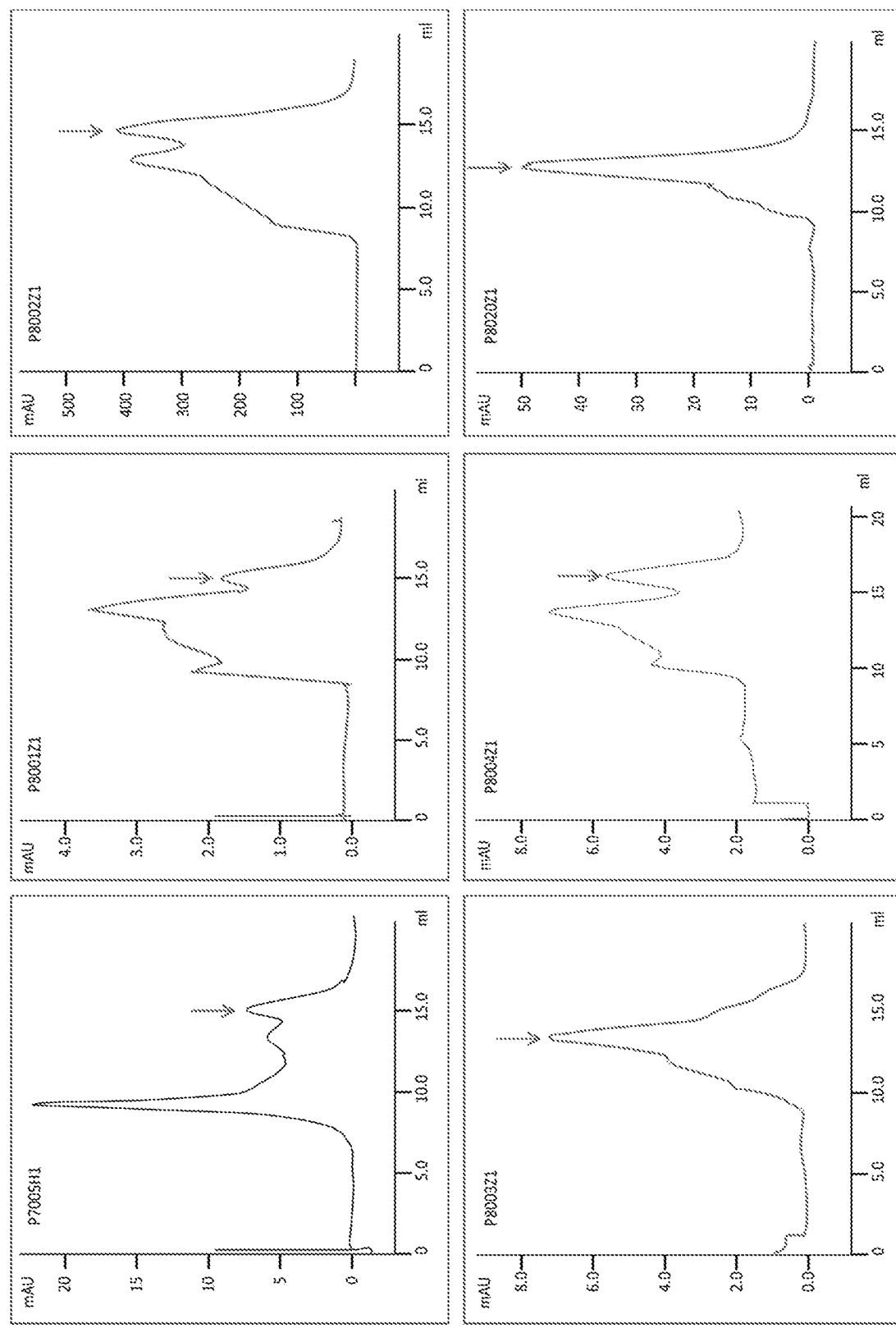
Figure 2. Size exclusion chromatographic analysis (SEC) of the rIVIG variants Figure 3. FcγR bindings of rIVIG molecules
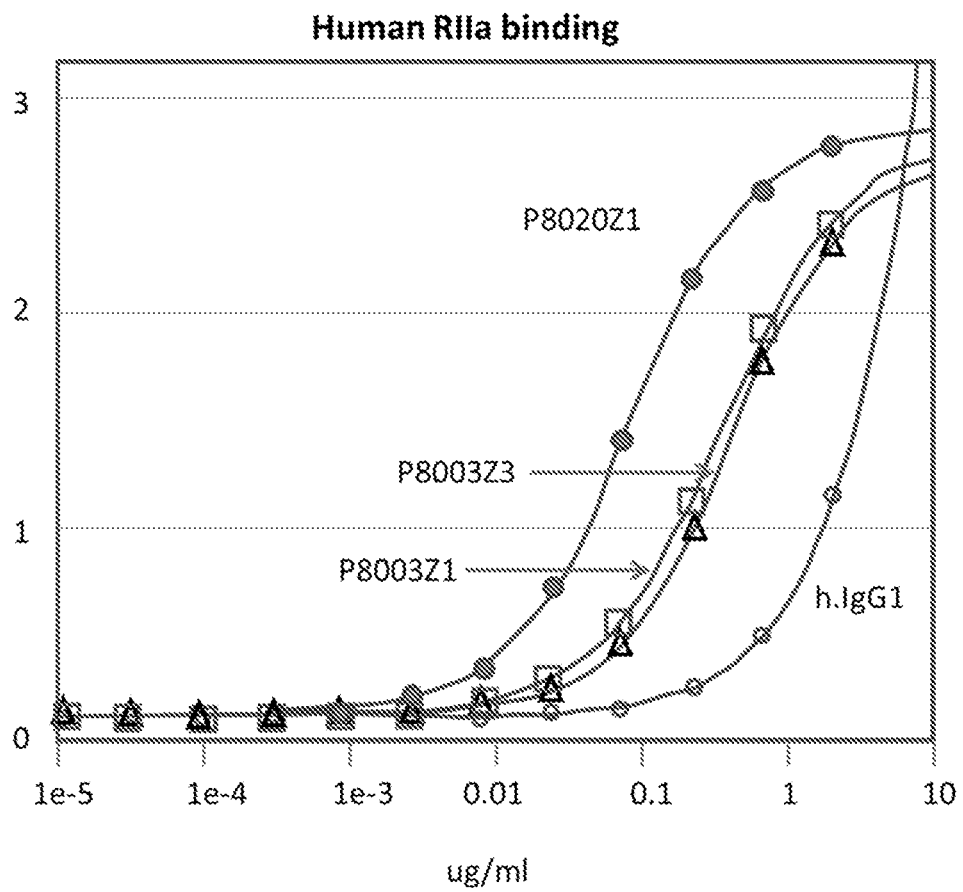
| KD in nM | Human Fc receptor | | | | | |
|---|---|---|---|---|---|---|
| | FcRI | FcRIIA[H] | FcRIIA[R] | FcRIIB | FcRIII | FcRn |
| IgG1 | 0.161 | 333 | 200 | 876 | 1183 | 14.0 |
| P8003Z1 | 0.15 | 0.5 | 0.19 | 2.81 | 2.78 | 0.37 |
| P8003Z3 | 0.13 | 0.36 | 0.17 | 2.45 | 0.17 | 0.43 |
| P8020Z1 | 0.07 | 0.7 | 0.18 | 0.64 | 1.03 | 0.44 |
| KD in nM | Mouse Fc receptor | | | |
|---|---|---|---|---|
| | FcRI | FcRIIB | FcRIII | FcRIV |
| IgG1 | 1.33 | 375 | N/A | 6.52 |
| P8003Z1 | 0.13 | 261 | 7.71 | 0.92 |
| P8003Z3 | 0.24 | 84 | 17.9 | 0.12 |
| P8020Z1 | 0.09 | 8.2 | 1.55 | 0.38 |

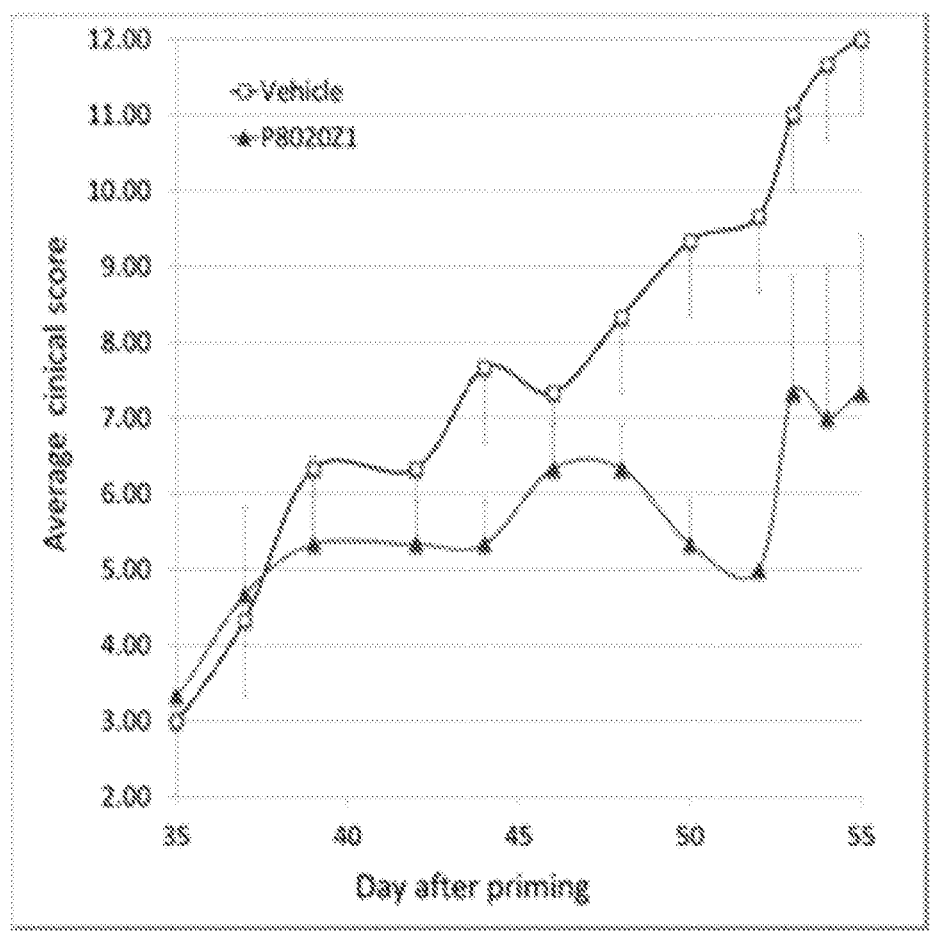
Figure 4. Therapeutic effects in CIA model

Figure 5. Therapeutic effects in CAIA model
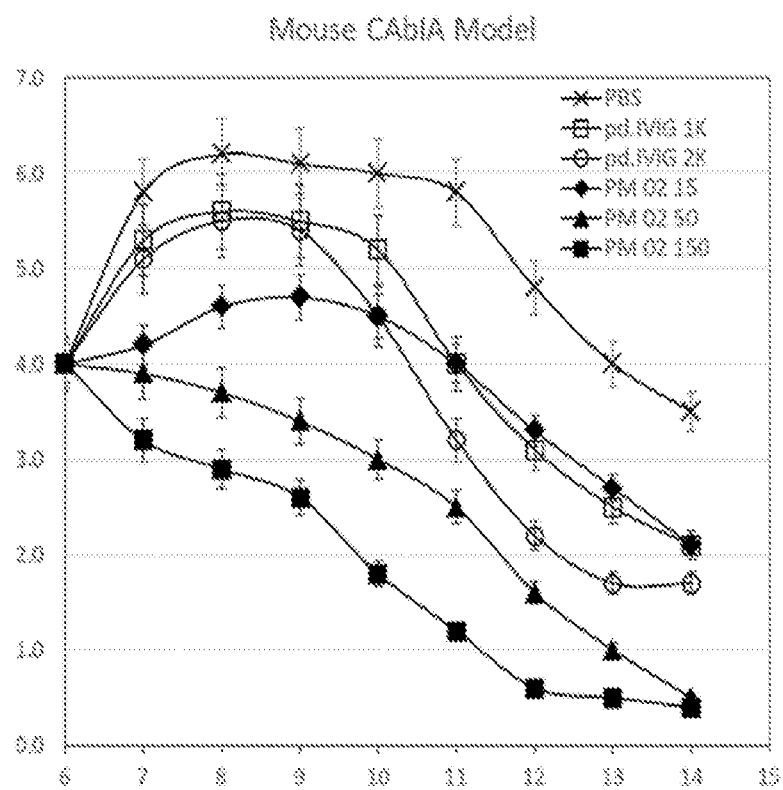
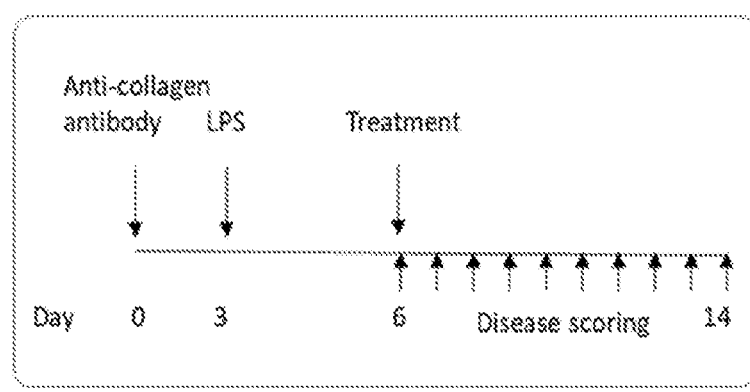

Figure 6. Size exclusion chromatographic profiles of P8003Z1 and P8020Z1

RECOMBINANT INTRAVENOUS IMMUNOGLOBULIN (RIVIG) COMPOSITIONS AND METHODS FOR THEIR PRODUCTION AND USE

STATEMENT OF RELATED APPLICATIONS

This application is a 35 U.S.C. § 371 National Stage Application of International Application No. PCT/US17/24650, filed on Mar. 29, 2017, which claims priority to U.S. provisional patent application Ser. No. 62/315,483, filed on Mar. 30, 2016, the entirety of which is hereby incorporated by reference.

SEQUENCE LISTING

The instant application contains a Sequence Listing which has been submitted electronically and is hereby incorporated by reference in its entirety. The file named "SHR-2003US_ST25.txt" was created on Sep. 27, 2018 and is 45,044 bytes in size.

FIELD OF THE INVENTION

The present invention relates to compositions and methods for the production of recombinant proteins which can be used as a substitute for current uses of human IVIG preparations (an acronym for intravenous immunoglobulins). The present invention further relates to methods of use of such compositions for the treatment of immunologic and other disorders and diseases.

BACKGROUND OF THE INVENTION

Clinical applications of immunoglobulin as a therapeutic agent dates back over one hundred years ago, when Emil Behring and colleague found immune serum can ameliorate toxin-mediated disease (1). Sixty two years passed before Ogden Bruton intravenously infused human immunoglobulins for immunoglobulin substitution in agammaglobulinemia patients (2). Until then, only limited doses of immunoglobulins could be administered intramuscularly, since the preparations contained aggregates of purified immunoglobulins, the administration of which led to painful local irritation and adverse systemic reactions due to activation of an immune response through the complement cascade (3, 4).

The development of new purification processes in the 1960s and 1970s allowed the removal of aggregates, making it possible to prepare compositions that were suitable for intravenous administration in a much larger dose (3-7). The acronym "IVIG" remains the commonly used term for such preparations, even though such preparations can also be administered through other modes, such as subcutaneous administration. The major indications for IVIG preparations remained primarily substitution therapy in patients with immunodeficiency (8-10).

In 1981, while treating a child with secondary immunodeficiency due to extensive immunosuppressive treatment, who also suffered with refractory immune thrombocytopenia (ITP), Paul Imbach found that the patient's platelet counts unexpected increased after the patient was treated with IVIG (11). The effect of IVIG treatment for increasing platelet counts was reproduced in ITP patients without immunodeficiency, and paved the path for IVIG usage for its immunomodulatory effects (12-15).

Currently, IVIG is a treatment option for many different diseases and is recommended as first line use as an immunomodulatory agent for a number of autoimmune disorders. In fact, while use of IVIGs as a substitute immunoglobulin in immune deficiency syndromes remains as an important indication, IVIGs are increasingly being used for treatment of autoimmune disorders.

Although IVIG preparations have been effective in clinical treatment, there are a number of issues associated with the current practice that may have a drastic impact to its sustainability. First, adverse effects are often observed following IVIG administration, including anaphylaxis, renal conditions, thrombotic complications, and diabetic conditions. Efforts taken to address these issues have included pre-screening of patients for IgA deficiency, as well as close monitoring of concentrations of IgA, factor XI, glucose, and sodium. However, each of these steps can have the effect of limiting the supplying capacity, and increasing the costs of goods, as well as costs of administration. Moreover, in spite of these efforts, IVIG usage continues to be disadvantaged by the adverse effects, which have not been completely ameliorated.

In addition, in contrast to most biologics, IVIG is normally administered at very high doses, generally ranging from about 0.5 g to 4 g per kg body weight. Judging from the dosage required for efficacy, it appears that the therapeutically active component(s) of IVIG account for only a very small portion of the preparation. With the significant challenges presented by the escalating costs of goods and the needs in improving the quality IVIG preparation, there is a significant need for improved alternative compositions and/or methods that will address one or more of these issues:

The issues presented by IVIG treatment stem in part from the fact that IVIG's mechanism of action has not been clearly determined, and its effects are likely to vary from indication to indication.

SUMMARY OF THE INVENTION

As described above, there is a significant need for improved treatment with IVIGs, including alternative(s) that can eliminate or reduce the adverse effects, and that can be produced with more consistent quality, allow for lower dosage while maintaining efficacy, and/or reduce the costs of goods. The inventors hypothesized that recombinant engineering of immunoglobulins would allow for the production of a better-defined molecule that can be produced with consistent quality, allow lower dosage while maintaining efficacy, and reduce costs of the good.

While the mechanism of action of IVIG is not completely clear, the present inventors hypothesized that it is possible to correlate at least some indications with the antibody structural elements that are required for IVIG's therapeutic efficacy in those indications. For example, in the treatment of immunodeficiency, IVIG replenishes levels of serum Ig and provides life-saving protection from infectious agents and/or their toxins. Hence, it is conceivable that the great diversity of the antigen-specificities contained within the variable regions of the pooled immunoglobulins are responsible for the therapeutic efficacy for these indications. In contrast, studies support the notion that it is the immunoglobulin Fc region that is responsible for IVIG's immunomodulatory effects in treatment of acute and chronic autoimmune disorders.

The observation was made that the intact IVIG and its Fc fragment have equivalent anti-inflammatory activity in treatment of ITP and in animal models (16). This would support the role of the Fc region in anti-inflammatory functions. In addition, it was observed that the immunomodulatory effects of IVIG are mediated through the Fc receptors and rely upon dendritic cell (DC)-macrophage cross-talk, and that the FcγRIIIa is critical for the activation phase and the FcγRIIb, for the effector phase in mouse ITP model (17). Lastly, the observation was made that in a mouse ITP model the treatment with IVIG containing a high content of Ig dimers reverses the platelet depletion much more effectively than that with normal monomeric immunoglobulin (18). Hence, the inventors theorized that the dendritic DC surface FcγRIIIa and FcγRIIb, which normally have low affinity binding for the Fc region, can productively interact with the small quantities of oligomeric antibodies present in IVIG preparations through the avidity (multiple interactions) binding that is provided by oligomeric Fc, which could be further utilized in order to improve upon the immunomodulatory effects of IVIG preparations.

The present invention provides methods and materials that fully or partially address the above concerns. Thus, in its broad aspect, the present invention comprises recombinant intravenous immunoglobulin (rIVIG) polypeptides comprising (a) a single chain Fc peptide comprising two or more Fc peptide domains; and (b) an oligomerization peptide domain. In a particular aspect of the present invention, the oligomerization peptide domain is a trimerization peptide domain. In particular embodiments, the rIVIG polypeptides of the present invention (also referred to as Pan Receptor Interacting Molecules, or "PRIM") comprise (a) a single-chain Fc peptide comprising two Fc peptide domains and (b) an oligomerization peptide domain, in particular, a trimerization peptide domain. The individual Fc peptide domains in the rIVIG polypeptides of the present invention may be joined via a flexible linker. In particular embodiments of the present invention, the flexible linker comprises five repeats of the amino acid sequence G-G-G-G-S(SEQUENCE ID NO: 9); i.e., G-G-G-G-S-G-G-G-G-S-G-G-G-G-S-G-G-G-G-S-G-G-G-G-S(SEQUENCE ID NO: 10). In other particular embodiments of the present invention, the oligomerization peptide domain comprises amino acid nos. 712 to 768 of SEQUENCE ID NO: 4, or amino acid nos. 1 to 79 of SEQUENCE ID NO: 6. In certain embodiments, the rIVIG polypeptide of the present invention comprises an amino acid sequence selected from the group consisting of SEQUENCE ID NO: 2, SEQUENCE ID NO: 3, SEQUENCE ID NO: 4, SEQUENCE ID NO: 5, SEQUENCE ID NO: 6, SEQUENCE ID NO: 7, and SEQUENCE ID NO: 8.

In other embodiments, the present invention comprises nucleotide molecules that encode recombinant intravenous immunoglobulin (rIVIG) polypeptides comprising (a) a single chain Fc peptide comprising two or more Fc peptide domains; and (b) an oligomerization peptide domain. In a particular aspect of the present invention, the nucleotide molecule encodes a trimerization peptide domain. In particular embodiments, the nucleotide molecule of the present invention encodes a rIVIG polypeptide comprising (a) two Fc peptide domains and (b) a trimerization domain. In particular embodiments, the present invention comprises a nucleotide molecule encoding a rIVIG polypeptide, which rIVIG polypeptide comprises an amino acid sequence selected from the group consisting of SEQUENCE ID NO: 2, SEQUENCE ID NO: 3, SEQUENCE ID NO: 4, SEQUENCE ID NO: 5, SEQUENCE ID NO: 6, SEQUENCE ID NO: 7, and SEQUENCE ID NO: 8.

In another aspect, the present invention provides compositions for treatment of immune disorders, said compositions comprising recombinant immunoglobulin (rIVIG) proteins, wherein said rIVIG proteins comprise an oligomerization peptide domain that provides a scaffold for bringing together three single chain Fc domains (scFc). In particular embodiments, the oligomerization peptide domain is comprises an amino acid sequence selected from the group comprising amino acids 1 to 79 of SEQUENCE ID NO: 6 and 712 to 768 of SEQUENCE ID NO: 4. In a particular aspect of the present invention, the composition comprises predominantly a single protein species comprising three single chain Fc peptides. The individual Fc domains of said single chain Fc peptides may interact intramolecularly to form functional single chain Fc peptides. In particular embodiments, the present invention provides compositions predominantly comprising a rIVIG protein, which rIVIG protein comprises an amino acid sequence selected from the group consisting of SEQUENCE ID NO: 2, SEQUENCE ID NO: 3, SEQUENCE ID NO: 4, SEQUENCE ID NO: 5, SEQUENCE ID NO: 6, SEQUENCE ID NO: 7, and SEQUENCE ID NO: 8.

In another aspect, the present invention provides a method of treating a patient suffering from an autoimmune disorder, said method comprising administering to said patient an effective amount of a composition predominantly comprising recombinant immunoglobulin (rIVIG) protein, wherein said rIVIG protein comprises an oligomerization peptide domain that provides a scaffold for the formation of trimers of a single chain Fc peptide. In a particular embodiment, the patient suffers from an immune disorder selected from refractory immune thrombocytopenia, immune thrombocytopenic purpura (ITP), chronic inflammatory demyelinating polyneuropathy (CIDP), multiple sclerosis (MS), system lupus erythematosus (SLE, or lupus), Graves Disease, Kawasaki disease, dermatomyositis, myasthenia gravis, Guillain-Barre syndrome, myasthenia gravis, autoimmune hemolytic anemia (IMHA), pernicious anemia, hemolytic anemia, aplastic anemia, paroxysmal nocturnal hemoglobinuria (PNH), Addison disease, Hashimoto's disease (chronic thyroiditis), Hashimoto's encephalopathy, autoimmune neutropenia, thrombocytopenia, rheumatoid arthritis and reactive arthritis, inflammatory bowel disease (IBD), ulcerative colitis, Crohn's disease, Sjögren syndrome, CREST syndrome, pelvic inflammatory disease (PID), ankylosing spondylitis, Behcet's disease, vasculitis, Lyme disease (chronic or late stage) and type I diabetes.

In another aspect, the present invention provides a method of reducing the immune rejection response of a patient who has received an organ transplant, bone marrow transplantation; blood transfusion, or stem cell transplantation, said method comprising administering to said patient an effective amount of a composition comprising recombinant immunoglobulin (rIVIG) protein, wherein said rIVIG protein comprises an oligomerization peptide domain that provides for a composition comprising predominantly trimers of single chain Fc peptides.

In another aspect, the present invention provides a method of treating a non-human mammal suffering from an autoimmune disorder, said method comprising administering to said non-human mammal an effective amount of a composition comprising recombinant intravenous immunoglobulin (rIVIG) protein, wherein said rIVIG protein comprises an oligomerization peptide domain that provides for a composition comprising predominantly trimers of single chain Fc peptides, and wherein said rIVIG protein comprises an amino acid sequence that has been derived from a non-human mammal of the same species. In particular embodiments, the non-human mammal suffers from an autoimmune disorder selected from the group consisting of autoimmune hemolytic anemia (AIHA), immune thrombocytopenia purpura (ITP), or rheumatoid arthritis. For example, a dog suffering from AIHA may be treated with a composition comprising predominantly trimeric rIVIG protein comprising an amino acid sequence of canine origin, such as the amino acid sequences of SEQUENCE ID NO: 7 and SEQUENCE ID NO: 8.

BRIEF DESCRIPTION OF THE FIGURES

FIG. 1 illustrates the composition of the constructs of certain embodiments of the present invention. P7005H is the prototype for the design for producing oligomeric functional Fc domains using the intrinsic trimerizing capacity of the extracellular domain of CD40 ligand. The smallest functional oligomers are made of six polypeptide chains that assembled into three dimeric Fc domains at the N-terminus and two trimerized CD40L ECD at the C-terminus. In light of the complex SEC profile (FIG. 2) of P7005H, the P8001Z was created in which the functional Fc domain was generated using the scFc format and the CD40L ECD was replaced by a collagen trimerizing domain. While the SEC profile (FIG. 2) is better than that of the P7005H, P8001Z still contains substantial amount of the higher order oligomers. As the similar construct, P8004Z, with additional human IgG1 heavy chain hinge region (H), also exhibited a less than ideal SEC profile, it appears that the inclusion of the hinge region alone would not solve the folding issue. Interestingly, when additional constant regions (CL and $CH_1$) were brought upon, both P8003Z and P8020Z proteins folded much more efficiently and exhibited as predominantly the properly folded trimer. (FIG. 2). (FIG. 2). The P8020Z construct employed a trimerizing scaffold which makes it possible to position the oligomeric Fc at the C-terminus of the fusion protein. The C-terminal Fc format is expected to closely mimic the orientation of a regular antibody for interacting with Fc receptors. Importantly, unlike P7005H, P8001Z, P8002Z or P8004Z, homogenous compositions of trimeric species were successfully obtained from expression of the P8003Z and P8020Z (See FIG. 5).

FIG. 2 illustrates the effects of a composition of the present invention in a size exclusion chromatography (SEC) profiling model. The rIVIG molecules of the present invention were purified by protein A affinity chromatography and buffer-exchanged into phosphate buffer saline, pH 7.2. Each SEC analysis was performed by injecting approximately 100 ul of the rIVIG sample at a speed of 0.5 ml/min using a Superdex 200 10/30 SEC column (GE Healthcare). The arrows indicate where the properly folded trimeric molecules are eluted. FIG. 2 shows that the less than about ⅓ of the P7005H, P8001Z, P8002Z and P8004Z are found to be in the properly folded trimeric form. In contrast, more than at least ⅔ of the P8003Z and P8020Z are properly folded as trimers. These results indicate that introduction of the CL and CH1 domains can greatly enhance the folding of the trimeric forms.

FIG. 3 illustrates the effects of a composition of the present invention in an FcγR binding model. Individual human Fc receptor fused with GST was coated on the ELISA plate. After blocking the unoccupied area, human IgG1, P8003Z1, P8003Z3 (afucosyl variant of P8003Z, produced from a cell line deficient of the alpha-1,6 fucosyl-transferase gene ($FUT8^{-/-}$)) or P8020Z1 was added to the plate at serial-diluted concentrations. The bound human IgG1 and rIVIG variants were quantified by fluorescent-labeled F(ab)'$_2$ fragment of goat anti-human antibody. The upper panel of FIG. 3 shows an example for the affinity measurement of human IgG1 and rIVIGs to human FcγRIIA (H131). The curve fitting (SoftMax Pro 5.1, Molecular Devices, Sunnyvale, Calif.) allows estimates of the KDs of the rIVIG to the recombinant soluble Fc receptors. Tables below shows these calculated KDs It is apparent that the trimeric rIVIGs of the present invention exhibit significant increases in binding affinities compared with human IgG1, with the exception of human FcγRI, to which human IgG1 already exhibits a sub-nM affinity and the rIVIGs exhibit only marginally higher affinities. These results substantiate that the trimeric rIVIGs of the present invention, with the avidity advantage, are able to bind to Fc receptor with much higher apparent affinities.

FIG. 4 illustrates the therapeutic effects of a composition of the present invention in a collagen induced arthritis (CIA) model. Mice were primed with bovine type II collagen in CFA on day 1, treated with P8020Z (50 mg/kg body weight) on day 18, and boosted with the same collagen in IFA on day 21. The clinical scores of 1 to 4, 4 being the most severe, of each paw was measured every other day. The clinical scores were added in each group and normalized by the number of mice. As a comparison to traditional human IVIG preparations which are regularly used at approximately 2-3 g/kg body weight and administered multiple times over the course of study, P8020Z1 was administered once with a dose of 50 mg/kg, representing a 40- to 60-fold reduction in dosing.

FIG. 5 illustrates the therapeutic effects of a composition of the present invention in an autoimmune disorder induced by passive transfer of anti-collagen antibodies. Mice were treated with anti-collagen antibody, with lipopolysaccharides 3 days after, and on day 6, with a single injection of either plasma derived IVIG (pd.IVIG) or the recombinant IVIG (rIVIG or PRIM) molecules (PM 02, also termed afucosyl P8003Z3) at the dose indicated. The dosing for pd.IVIG 1K is 1 gm per kg of body weight; for pd.IVIG 2K, the dose is 2 gm per kg body weight. PM02 15 is 15 mg per kg body weight; PM 02 50 is 50 mg per kg body weight; and PM 02 150 is 150 mg per kg body weight. Both pd.IVIG 1K and pd.IVIG 2K are slightly more efficacious between day 9 and day 13. PM 02 15 exhibits a comparable therapeutic efficacy as both concentrations of pd.IVIG. PM 02 50 and PM02 150 both exhibit much better efficacy than either pd.IVIG dosing. Hence, PM 02 is demonstrated to be capable of treating an autoimmune disorder induced by passive transfer of anti-collagen antibodies.

DETAILED DESCRIPTION OF THE INVENTION

Figure 6A:
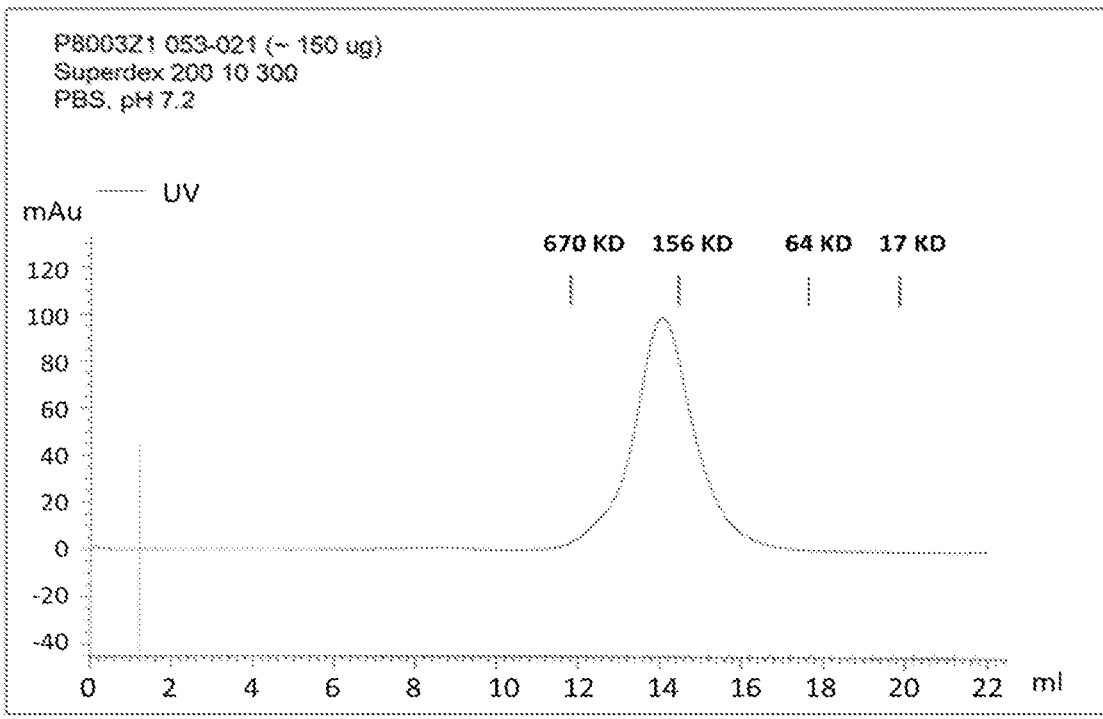
FIG. 6 illustrates the size exclusion chromatographic profile of P8003Z1 and P8020Z1. The peak representing the trimeric rIVIG protein of the present invention demonstrates that the rIVIG peptides of the present invention can be made in homogeneous form.
Figure 6B:
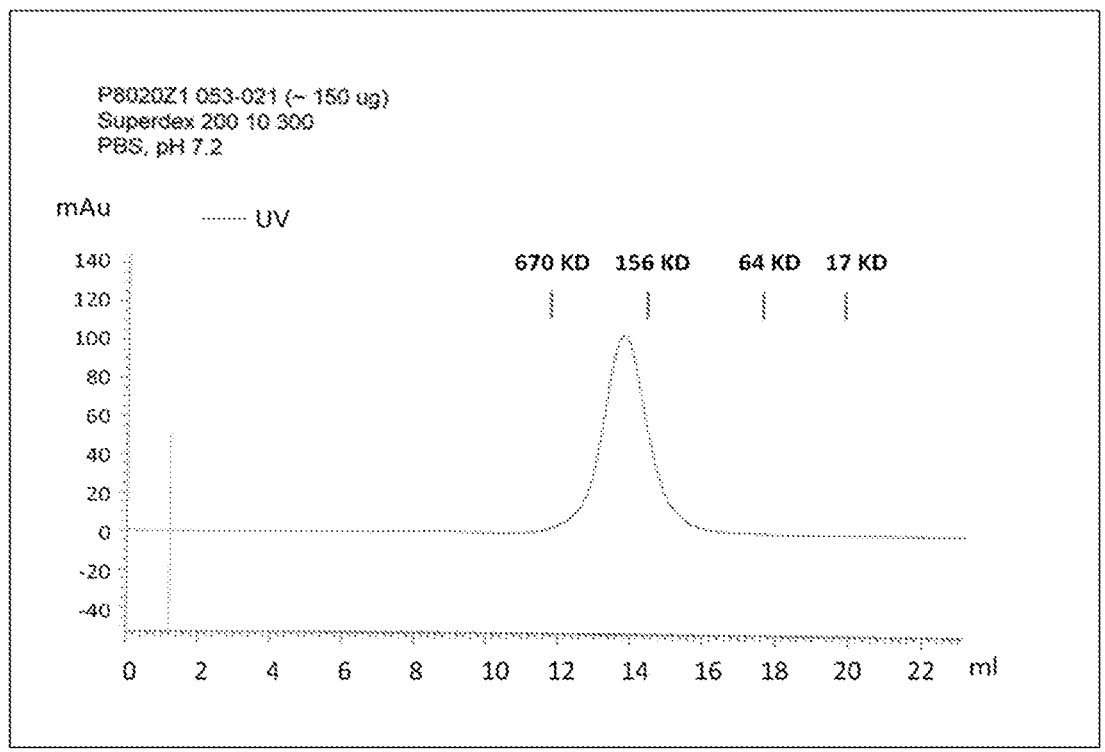

In the following description, for the purposes of explanations, numerous specific details are set forth in order to provide a thorough understanding of the present invention. It will be apparent, however, to one of ordinary skill in the art, that the present invention may be practiced without these specific details, and that various modifications and changes may be made thereto without departing from the broader scope of the invention.

All publications which are cited herein are hereby specifically incorporated by reference into the disclosure for the teachings for which they are cited.

As used herein, the term 'subject' refers to mammals and non-mammals Mammals refers to any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like.

The present invention is directed towards recombinant intravenous immunoglobulin (rIVIG) proteins, compositions comprising such rIVIGs, and methods for the production, purification and use of compositions of rIVIGs for the treatment of various immunological disorders and conditions.

In the present invention, the design of recombinant immunoglobulins (rIVIG) focuses on engineering of nucleic acid and protein molecules containing multiple copies of the human IgG1 Fc domain, together with domains that enhance the formation of oligomerized rIVIG molecules. While not wishing to be bound by any theory, it is expected that the rIVIG molecules of the present invention are capable of binding not only to the high affinity FcγRI, but also to the low affinity Fc receptors, namely, the FcγRII and FcγRIII receptors. The enhanced binding of the low affinity receptor is most likely due to the avidity interaction of the oligomeric Fc with the Fc receptors present on the cell surface.

Biochemically, the present invention provides methods and materials which are designed to bring together the Fc domain and an oligomerizing protein scaffold in order to generate a fusion protein that is properly folded and exhibits desirable characteristics for use as a therapeutic product. Therapeutically, the rIVIG proteins of the present invention are useful for the treatment of a number of immunological conditions, and as an immunomodulatory agent for a number of autoimmune disorders. Furthermore, considering that various complement proteins are involved in many autoimmune disorders, the present invention may optionally include additional structural elements, for example, elements that are capable of scavenging components along the complement activation cascade.

The present inventors have designed and expressed a number of rIVIG molecules using a variety of protein scaffolds to oligomerize variants of Fc constructs. In certain preferred embodiments, the rIVIG molecules of the present invention comprise oligomeric scaffold domains that preferentially bring together three single chain Fc peptides or three Fc dimers to form three functional Fc domains.

The methods and materials of the present invention are useful to treat immune disorders, including but not limited to autoimmune diseases, or any disorder, disease or syndrome where immunomodulation is desired. Indications for which the present invention can be used include, but are not limited to, immune thrombocytopenic purpura (ITP), chronic inflammatory demyelinating polyneuropathy (CIDP), multiple sclerosis (MS), system lupus erythematosus (SLE, or lupus), Graves Disease, Kawasaki disease, Addison disease, Celiac-disease-sprue, dermatomyositis, myasthenia gravis, dermatitis, Hashimoto's disease (chronic thyroiditis), Hashimoto's encephalopathy, Guillain-Barre syndrome, myasthenia gravis, autoimmune hemolytic anemia (IMHA), pernicious anemia, hemolytic anemia, aplastic anemia, paroxysmal nocturnal hemoglobinuria (PNH), autoimmune neutropenia, thrombocytopenia, rheumatoid arthritis and reactive arthritis, inflammatory bowel disease (IBD), ulcerative colitis, Crohn's disease, Sjögren syndrome, CREST syndrome, pelvic inflammatory disease (PID), ankylosing spondylitis, Behcet's disease, vasculitis, Lyme disease (chronic or late stage) and type I diabetes.

The methods and materials of the present invention are also useful for the treatment of disorders caused by autoantibodies, as well as organ specific autoimmune disorders, including myocarditis, post-myocardial infarction syndrome nephritis, Goodpasture syndrome, interstitial cystitis, autoimmune hepatitis, primary biliary cirrhosis and primary sclerosing cholangitis (PSC), antisynthetase syndrome; alopecia areata, autoimmune angioedema, dermatitis, psoriasis, systemic scleroderma, lymphoproliferative syndrome, antiphospholipid syndrome, autoimmune retinopathy, uveitis, and Meniere's disease.

The methods and materials of the present invention are also useful for the prevention, reduction and/or treatment of immune or antibody-mediated reactions to procedures including organ transplant, bone marrow transplantation; blood transfusions, or stem cell transplantation.

The methods and materials of the present invention can also be used for any autoimmune indications where any commercially available intravenous immunoglobins (IVIG) have been used. Commercially available IVIGs include: Carimune®, Flebogamma®, Gammagard,®, Gammaked™, Gammaplex, Gamunex®-C, Octagam® and Privigen®. Specific uses and autoimmune indications for which commercially available IVIGs have been approved include the following: chronic inflammatory demyelinating polyneuropathy (CIDP); chronic immune thrombocytopenic purpura (ITP); multifocal motor neuropathy (MMN); control of bleeding in ITP; and prevention of coronary artery aneurysms associated with Kawasaki syndrome in pediatric patients.

The present invention comprises recombinant IVIG (rIVIG) proteins that can be expressed and purified as a homogeneous species containing three functional scFc domains. This trimeric Fc oligomer can bind to both high affinity and low affinity Fc receptors due to the avidity (multiple valence) interactions. These enhanced affinities toward various Fc receptors are reminiscent of the small amount of the oligomerized antibodies present in preparations of human IVIG which have been attributed to the immunomodulatory effects of human IVIG. Due to its mimicry in enhanced interaction with Fc receptors, the rIVIG of current invention is expected to replace the traditional IVIG for its immunomodulatory application and not for its passive immune protection application.

Immunoglobulins
Fc Fragments

The present invention utilizes CH2-CH3 domains that comprise the human heavy chain constant region 2 (CH2) and constant region 3 (CH3) of IgG (CH2-CH3), preferably IgG1. When two or more Fc fragments, such as CH2-CH3 domains are used, they are generally synthesized or expressed in the form of a single chain Fc peptide in which the CH2-CH3 domains are linked using a flexible peptide linker, such as (GGGGS)$_5$ (=GGGGSGGGGSGGG-GSGGGGSGGGGS (SEQUENCE ID NO: 10)), which favors intramolecular interactions between the separate CH2-CH3 domains of the single chain Fc peptide, allowing the single chain Fc peptide to assume a three dimensional conformation that optimizes biological function. A hinge region (H) from human IgG, preferably IgG1, may also be present at the N-terminal end of each CH2 region to encourage the proper conformation to optimize biological activity.

In certain embodiments, the rIVIG proteins of the present invention include further regions of the Fc molecule. For example, the rIVIG can include one or more constant region 1 (CH1) domains of IgG, preferably IgG1, as well as one or more Ig kappa or light chain constant region (CL) domains. The C-terminal end of the CL domain can be linked to the N-terminus of the CH1 domain, using a short linker sequence, such as (GGGGS)$_2$. In this construct, the CH1 domain can interact with the CL domain through an intra-molecular disulfide linkage which is thermodynamically much more favorable than that of an inter-molecular disulfide linkage. In addition, the CL/CH1 domain plays a role in scavenging complement components, which can further ameliorate the complement immune response that is present in many autoimmune disorders.

Human Antibody Isotypes

It is known that several different isotypes of antibody exist, which have different binding patterns, leading to distinct functional roles in the body. The binding affinities for each isotype are generally known (Gillis et al. (2014) Frontier Immunology 5:1-13), and are shown in Table 1 below. The Fc of each antibody isotype binds to Fc receptor differently. For example, the binding affinity of human IgG3 to FcγRIIIA (0.1 micro-molar (uM) KD) is at least 50× higher than that of human IgG1 to the same receptor (5-10 uM KD). Similarly binding of human IgG1 to FcγRIIA is 15× stronger than that of human IgG4. Accordingly, although the examples herein use Fc fragments derived from IgG1, Fc fragments from each isotype can be used in the present invention. For example, variants of P8003Z or P8020Z carrying constant regions of IgG2, IgG3, or IgG4 isotype are expected to exhibit different affinity from that of the parental P8003Z or P8020Z which carry the constant regions of IgG1 isotype. Since many autoimmune disorders are associated with differentially combined expression of Fc receptors, rIVIGs of the present invention derived from each isotype variant may offer distinct therapeutic benefits.

also known to play a critical role in the Fc-Fc receptor interactions. In fact, it is clear that alterations of glycoforms at Asn-297 residue occur under physiological and pathological conditions (23). In addition, differential sialylation has been reported to affect the inflammatory properties of IgG and has been proposed as a mechanism of a molecular switch to induce an anti-inflammatory condition (24). Furthermore, removal of the glycan entirely compromises the ability of Fc to interact with all Fc receptors except the neonatal Fc receptor (FcRn) (25). Most interestingly, it has been found that elimination of the core fucose in the N-glycan complex leads to up to 100× selective enhancement of Fc to the FcγRIII interaction (26). The non-fucosylated form of antibody can be produced by expressing the very same antibody in a host cell line that is deficient of the alpha-1,6 fucosyltransferase gene (FUT8$^{-/-}$). The P8003Z1 and P8003Z3 differ in the core fucosyl saccharide in that the P8003Z1 is produced in the FUT8 competent cells, and the P8003Z3 in FUT8-deficient cells. The non-fucosylated P8003Z3 exhibits an enhanced binding to human FcγRIII and murine FcγRIV as expected (see the KD Table in FIG. 3).

Thus, as will be apparent to the skilled artisan, rIVIG proteins with modified glycosylation, cell lines and culture media that produce rIVIG proteins with modified glycosylation, can be used in the present invention, and their use for production of rIVIGs and the use of rIVIG proteins with modified glycosylation in therapeutic treatment of immune disorders forms a part of the present invention.

Oligomerization Scaffold Domains

As used herein, the terms "oligomerization domain" "oligomerization scaffold domain," and "oligomerizing protein scaffold" are used interchangeably to indicate that the specified sequence functions to form oligomeric structures. The oligomerization scaffold domains useful in the present

TABLE 1

Affinity of Human Antibody Isotypes to Fc Receptors

| | | KD in uM | | | | | | | |
|---|---|---|---|---|---|---|---|---|---|
| | FcγR1 | FcγRIIA | | FcγRIIB | | FcγRIIC | FcγRIII | | FcγRIIIb | FcRn |
| Allotype | — | H131 | R131 | I232 | T232 | — | V158 | F158 | NA1, NA2 | — |
| IgG1 | 0.017 | 2.00 | 0.33 | 10.00 | ND | 10.00 | 5.00 | 10.00 | 5.00 | 0.013 |
| IgG2 | — | 2.50 | 10.00 | 50.00 | ND | 50.00 | 14.29 | 33.33 | — | 0.020 |
| IgG3 | 0.017 | 1.11 | 1.11 | 5.00 | ND | 5.00 | 0.10 | 0.13 | 1.00 | 0.033 |
| IgG4 | 0.033 | 5.00 | 5.00 | 5.00 | ND | 5.00 | 5.00 | 5.00 | 5.00 | 0.050 |

Non-Human Mammalian Antibody Subclasses

Certain non-human mammalian species are known to have subclasses of antibodies that are analogous to human antibody isotypes. For example, there are four known subclasses of canine immunoglogulins: subclass A, subclass B, subclass C and subclass D, respectively. The subclasses share functional properties with the four human IgG isotypes. It has been reported that canine subclasses A and D appear effector-function negative while subclasses B and C bind canine Fc gamma receptors and are positive for ADCC. It has further been reported that all canine subclasses bind the neonatal Fc receptor except subclass C (22).

Glycosylation of Immunoglobulin Fc Domain and Enhanced Interaction of Afucoysl Antibodies to FcγRIII (Human) and FcγRIV.

In addition to the isotype difference, the differential glycosylation at the single glycosylation site (Asn-297) is invention include those that will induce trimerization of its fusion partner such as single chain Fc peptides, forming a trimeric rIVIG molecule, in which each rIVIG molecule comprises two H-CH2-CH3 Fc domains (hinge region-heavy chain constant region 2-heavy chain constant region 3). In certain embodiments, such as exemplified by P8020Z (SEQUENCE ID NO: 6), the oligomerization scaffold domain can be at the N-terminus of the construct, in which case the C-terminal end of the oligomerization scaffold domain can be linked to the N-terminal end of the first hinge region (H) or CH2 region, or the CL domain, directly or indirectly through a short linker sequence, such as GGGGS. In other embodiments, such as exemplified by P8003Z (SEQUENCE ID NO: 4), the oligomerization scaffold domain can be at the C-terminal end of the construct in which case the N terminal end of the oligomerization scaffold domain can be linked to the C-terminal end of the last CH3 domain, directly or indirectly through a short linker sequence, such as GGGGS (SEQUENCE ID NO: 9).

Linkers and Flexible Linkers

The linkers and flexible linkers useful in the present invention include glycine- and/or serine-rich peptide linkers, having a plurality of glycine or serine residues and defining a polypeptide of a length sufficient to span the distance between the C-terminal end of the first domain and the N-terminal end of the second domain. The term "flexible linker" is used to define a polypeptide sequence of sufficient length to allow the formation of a flexible, unstructured polypeptide configuration essentially free of secondary structure in aqueous solution, and provide the means for joining two protein domains, so that a chimeric or fusion protein can be produced as a single polypeptide molecule from a single nucleic acid construct.

The linker can vary in length, so as to allow in a manner that allow intramolecular interaction between the separate domains, thereby allowing formation of three dimensional conformations that optimize biological function. As used herein, the term "flexible linker" is generally applied to linkers having ten or more amino acids in length. Suitable flexible linkers generally are of a length of at least ten amino acid residues, and include linker polypeptides having from about 10 up to about thirty-six amino acid residues. Preferred flexible linkers are those that have greater than at least about 50% glycine residues and from about 10 to about 30 amino acids in length; more preferably from about 12 to about 25 amino acids in length, or from about 15 to about 25 amino acids in length. Flexible linkers useful in the present invention include, for example, an amino acid sequence of $(GGGGS)_n$; where n is from 2 to 7. The term "G4S" is used interchangeably to refer to sequence GGGGS (SEQUENCE ID NO: 9. Preferred flexible linkers include amino acid sequences of $(GGGGS)_n$; where n is from 2 to 6; and more preferably n is from 3 to 5. Such glycine-rich and/or serine-rich peptide linkers are well known and have been used to join antibody domains to form single chain Fv (sFv) proteins that incorporate a complete antibody binding site into a single polypeptide chain Serine-rich and/or glycine-rich peptide linkers of less than twelve amino acid residues can also be used as linkers to join peptide domains, but do not generally provide sufficient flexibility to allow conformations in which adjacent fusion peptide domains can interact intramolecularly. A particular flexible linker that can be used in the present invention comprises the amino acid sequence $(GGGGS)_5$ (SEQUENCE ID NO: 9). Shorter linkers that are useful in the present invention, where a flexible linker is not desired, include linkers that comprise the amino acid GGGGS and $(GGGGS)_2$. Generally, the linkers may comprise other amino acid residues having unreactive side chains, such as alanine, and threonine. However, the linkers should generally be free of charged amino acid residues and free of cysteine residues, which can form disulfide linkages. Suitable flexible peptide linkers, and DNA constructs useful for their production, are described in U.S. Pat. Nos. 5,258, 498; 5,482,858; and 5,525,491.

Purification:

The present invention is further directed towards compositions predominantly comprising one or more rIVIG proteins of the present invention. As used herein, when used with respect to the weight of a composition, the term "predominantly comprising" one or more rIVIG proteins means that a composition comprises at least 50%, at least 55%, at least 60%, at least 65%, at least 70%, at least 75%, at least 80%, at least 85%, at least 90%, or at least 95%, of the specified rIVIG proteins by weight of the total composition weight. When used with respect to the amount of protein in a composition, the term "predominantly comprising" one or more rIVIG proteins means that a composition comprises, by mole percent, at least 50%, at least 55%, at least 60%, at least 65%, at least 70%, at least 75%, at least 80%, at least 85%, at least 90%, or at least 95% of the specified rIVIG proteins by mole percent of the total protein present in the composition by mole percent.

Compositions predominantly comprising one or more rIVIG proteins of the present invention may be obtained using traditional methods of purification of IgG, using Protein A-Agarose, which binds to the Fc portion of IgG or Protein G-Agarose, which binds preferentially to the Fc portion of IgG, but can also bind to the Fab region of IgG, making it useful for purification of F(ab')2. Additional purification methods which are known in the art can be used for further purification of compositions of rIVIG proteins according to the present invention, including size exclusion chromatography (SEC) and hydrophobic interaction chromatography (HIC). See http://www.kpl.com/docs/techdocs/purifigg.pdf (accessed Mar. 23, 2016), and references cited therein; Surolia et al. (1982) Trends Biochem. Sci. 7:74-76; Harlow and Lane, eds. (1988) Antibodies, A Laboratory Manual (Cold Spring Harbor Laboratory, NY), p. 617-618; Langone (1982) J. Immunological Methods 55:277-296; Lindmark et al. (1983) J. Immunological Methods 62:1-13; and Thruston and Henley (1988) in Walker, ed. Methods in Molecular Biology, Vol. 3—New Protein Techniques (Humana. Press: Clifton, N.J.) p. 149-158.

Compositions

The present invention is further directed towards compositions of rIVIG proteins which have been combined with a pharmaceutically acceptable adjuvant or carrier. As used, the term "pharmaceutically acceptable" means acceptable for use in the pharmaceutical arts, i.e. not being unacceptably toxic, or otherwise unsuitable for administration to a mammal. Examples of pharmaceutically acceptable adjuvants include, but are not limited to, diluents, excipients and the like. Reference may be made to "Remington's: The Science and Practice of Pharmacy", 21st Ed., Lippincott Williams & Wilkins, 2005, for guidance on drug formulations generally.

The pharmaceutical compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution may include polyquaternium-1, benzalkonium chloride, thimerosal, chlorobutanol, methyl paraben, propyl paraben, phenylethyl alcohol, disodium-EDTA, sorbic acid, benzethonium chloride, and the like. Typically (but not necessarily) such preservatives are employed at a level of from 0.001% to 1.0% by weight.

Typically (but not necessarily) buffers are employed in order to maintain the formulation at or close to physiological pH. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents include dextran 40, dextran 70, dextrose, glycerin, potassium chloride, propylene glycol, sodium chloride, and the like, such that the sodium chloride equivalent of the injectable solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The selection of adjuvant depends on the intended mode of administration of the composition, and may also take into account the intended indication and patient. In one embodiment of the invention, the compounds are formulated for administration by infusion, or by injection either subcutaneously or intravenously, and accordingly may be utilized as aqueous solutions in sterile and pyrogen-free form and optionally buffered or made isotonic. Thus, the compounds may be administered in distilled water or, more desirably, in saline, phosphate-buffered saline or 5% dextrose solution. In addition to the foregoing, formulations of the present invention may further comprise additional active ingredients and/or inactive ingredients, including solvents, diluents, suspension aids, thickening or emulsifying agents, binders, stabilizers, lubricants and the like, as suited to the particular dosage and mode of administration. Except insofar as any conventional carrier medium is incompatible with the ingredients of the invention, such as by producing any undesirable effect or otherwise interacting in a deleterious manner with any other ingredient(s) of the formulation, its use is contemplated to be within the scope of this invention.

Methods of Administration:

The pharmaceutical compositions may be suitable for a variety of modes of administration described herein, including for example systemic or localized administration. The pharmaceutical compositions can be in the form of injectable solutions or in a form suitable for oral administration. The pharmaceutical compositions described herein can be packaged in single unit dosages or in multidosage forms. In certain embodiments, the pharmaceutical compositions are suitable for administration to an individual, a vertebrate, a mammal, or a human by any route of administration described herein, including oral administration or intravenous injection.

The compositions described herein can be administered to an individual via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular, intrathecal, transdermal, transpleural, intraarterial, topical, inhalational (e.g., as mists of sprays), mucosal (such as via nasal mucosa), subcutaneous, transdermal, gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection).

In some embodiments, the compositions are administered intravascularly, such as intravenously or intraarterially. In some embodiments (for example for the treatment of renal diseases), the compositions are administered directly into arteries (such as renal arteries). In preferred embodiments, the compositions are administered subcutaneously.

In some embodiments, the compositions may be administered directly to the eye or the eye tissue. In some embodiments, the compositions are administered topically to the eye, for example, in eye drops. In some embodiments, the compositions are administered by injection to the eye (intraocular injection) or to the tissues associated with the eye. The compositions can be administered, for example, by intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. These methods are known in the art. For example, for a description of exemplary periocular routes for retinal drug delivery, see Periocular routes for retinal drug delivery, Raghava et al. (2004), Expert Opin. Drug Deliv. 1(1):99-114. The compositions may be administered, for example, to the vitreous, aqueous humor, sclera, conjunctiva, the area between the sclera and conjunctiva, the retina choroids tissues, macula, or other area in or proximate to the eye of an individual.

The compositions can also be administered to the individual as an implant. Preferred implants are biocompatible and/or biodegradable sustained release formulations which gradually release the compounds over a period of time. Ocular implants for drug delivery are well-known in the art. See, e.g., U.S. Pat. Nos. 5,501,856, 5,476,511, and 6,331, 313. The compositions can also be administered to the individual using iontophoresis, including, but are not limited to, the ionophoretic methods described in U.S. Pat. No. 4,454,151 and US 2003/0181531 and 2004/0058313.

Dosage:

The optimal effective amount of the compositions can be determined empirically and will depend on the type and severity of the disease, route of administration, disease progression and health, mass and body area of the individual. Such determinations are within the skill of one in the art. The effective amount can also be determined based on in vitro assays. Examples of dosages of the composition which can be used for methods described herein include, but are not limited to, an effective amount within the dosage range of any of about 0.01 ug/kg to about 300 mg/kg, or within about 0.1 ug/kg to about 40 mg/kg, or with about 1 ug/kg to about 20 mg/kg, or within about 1 ug/kg to about 10 mg/kg. For example, when administered subcutaneously, the composition may be administered at low microgram ranges, including for example about 0.1 ug/kg or less, about 0.05 ug/kg or less, or 0.01 ug/kg or less. In some embodiments, the amount of composition administered to an individual is about 10 ug to about 500 mg per dose, including for example any of about 10 ug to about 50 ug, about 50 ug to about 100 ug, about 100 ug to about 200 ug, about 200 ug to about 300 ug, about 300 ug to about 500 ug, about 500 ug to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose.

The compositions may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgical implanted in various locations in the body.

Co-Administration

The present invention provides methods for the improved treatment of an immune disorder or disease, comprising co-administering a rIVIG composition of the present invention with one or more additional active agent that has prophylactic or therapeutic activity, or has been approved for use as a treatment for such immune disorder or disease. In such methods, the rIVIG composition may be administered prior to, simultaneously or after administration of the additional active agent. For example, in the treatment of rheumatoid arthritis (RA), a rIVIG composition of the present invention may be co-administered with a composition comprising Humira® (adilimumab, AbbVie Inc.), a therapeutic antibody that is approved for use in RA. It is expected that the rIVIG composition will provide additional relief for a patient suffering from RA, and that the effects of the rIVIG composition may be synergistic with those of Humira®.

The present invention provides methods for the improved treatment of patients who have received an organ transplant, or other procedure such as stem cell transplantation or blood transfusion, comprising administering a rIVIG composition of the present invention prior to, simultaneously with or after such transplant or other procedure. Such treatment according to the present invention provides methods for preventing or reducing an antibody-mediated immune response (i.e., immune rejection) against the transplanted organ. The rIVIG composition may be co-administered with one or more additional active agents that has prophylactic or therapeutic activity against such antibody-mediated immune response or rejection of the transplanted organ.

For example, in the treatment of kidney transplant recipients, a rIVIG composition of the present invention may be co-administered with a composition comprising an immunosuppressant drug such as cyclosporine. Other immunosuppressant drugs that may be co-administered with the compositions of the present invention include calcineurin inhibitors such as tacrolimus; mTOR inhibitors such as sirolimus; antiproliferative agents, such as mycophenolate and azathioprine; and steroids, such as prednisone. It is expected that the rIVIG composition will provide additional relief for a patient suffering from immune rejection, and that the effects of the rIVIG composition may be synergistic with those of immunosuppressant agents. Additionally, such treatment according to the present invention may allow reducing the amount of such immunosuppressant agents.

Coding Nucleotide Molecules, Recombinant Vectors and Recombinant Cell Lines

Methods of synthesizing nucleotide molecules that encode rIVIG proteins of the present invention are known in the art. Using the genetic code, the amino acid sequences of the rIVIG proteins of the present invention can be readily reverse-translated and codon-optimized using on-line tools (27); and the coding nucleotide molecules may be synthesized using strategies such as the hierarchical method of gene synthesis described in Kim et al. (28).

For the expression of rIVIG proteins of the present invention, it is known that the coding nucleotide sequence can be expressed in host cells using recombinant vectors, in which the nucleic acid sequence encoding a rIVIG protein is under the control of a suitable promoter that will drive expression of the rIVIG protein in the host cell. Suitable host cells include, for example, mammalian CHO cells, 293T cells (29).

Gene Therapy

The molecules can also be delivered by expression of the fusion protein in vivo, which is often referred to as "gene therapy." For example, cells may be engineered with a polynucleotide (DNA or RNA) encoding for the fusion protein ex vivo, the engineered cells are then provided to an individual to be treated with the fusion protein. Such methods are well-known in the art. For example, cells may be engineered by procedures known in the art by use of a retroviral particle containing RNA encoding for the fusion protein of the present invention. Local delivery of the rIVIG proteins of the present invention using gene therapy may provide the therapeutic agent to a localized target area.

Methods of gene delivery are known in the art. These methods include, but are not limited to, direct DNA transfer, see, e.g., Wolff et al. (1990) Science 247: 1465-1468; 2) Liposome-mediated DNA transfer, see, e.g., Caplen et al. (1995) Nature Med. 3:39-46; Crystal (1995) Nature Med. 1:15-17; Gao and Huang (1991) Biochem. Biophys. Res. Comm. 179:280-285; 3) Retrovirus-mediated DNA transfer, see, e.g., Kay et al. (1993) Science 262:117-119; Anderson (1992) Science 256:808-813; 4) DNA Virus-mediated DNA transfer. Such DNA viruses include adenoviruses (preferably Ad2 or Ad5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al. (1994) Gene Therapy 1:367-384; U.S. Pat. No. 4,797,368, incorporated herein by reference, and U.S. Pat. No. 5,139,941.

Retroviruses from which the retroviral plasmid vectors hereinabove mentioned may be derived include, but are not limited to, Moloney Mouse Leukemia Virus, spleen necrosis virus, retroviruses such as Rotis Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Mouse Leukemia Virus.

Adenoviruses have the advantage that they have a broad host range, can infect quiescent or terminally differentiated cells, such as neurons or hepatocytes, and appear essentially non-oncogenic. See, e.g., Ali et al. (1994), supra, p. 367. Adenoviruses do not appear to integrate into the host genome. Because they exist extrachromosomally, the risk of insertional mutagenesis is greatly reduced. Ali et al. (1994), supra, p. 373.

Adeno-associated viruses exhibit similar advantages as adenoviral-based vectors. However, AAVs exhibit site-specific integration on human chromosome 19 (Ali et al. (1994), supra, p. 377).

The gene therapy vectors may include one or more promoters. In some embodiments, the vector has a promoter that drives expression in multiple cell types. In some embodiments, the vector has a promoter that drives expression in specific cell types (such as cells of retina or cells in the kidney). Suitable promoters which may be employed include, but are not limited to, the retroviral LTR; the SV40 promoter; and the human cytomegalovirus (CVM) promoter described in Miller et al. (1989) Biotechniques 7(9):980-990, or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding a rIVIG protein is preferably under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoA1 promoter; human globin promoters; viral thymidine kinase promoters, such as the Herpes Simplex thymidine kinase promoter; retroviral LTRs (including the modified retroviral LTRs hereinabove described); the .beta.-actin promoter; and human growth hormone promoter.

Retroviral plasmid vectors can be employed to transduce packaging cell lines to form producer cell lines. Examples of packaging cells which maybe transfected are described in Miller (1990) Human Gene Therapy 1:5-14. The vectors may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host. The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Ex Vivo Administration

In some embodiments, the immunomodulatory effect of the rIVIG protein can be achieved by contacting a body fluid with a composition comprising a molecule ex vivo under conditions that permit the molecule to function to modulate immune response. Suitable body fluids include those that can be returned to the individual, such as blood, plasma, or lymph. Affinity adsorption apheresis is described generally in Nilsson et al. (1988) Blood 58(1):38-44; Christie et al. (1993) Transfusion 33:234-242; Richter et al. (1997) ASAIO J. 43(1):53-59; Suzuki et al. (1994) Autoimmunity 19: 105-112; U.S. Pat. No. 5,733,254; Richter et al. (1993) Metabol. Clin. Exp. 42:888-894; and Wallukat et al. (1996) Int'l J. Card. 54:1910195.

Accordingly, the invention includes methods of treating one or more diseases described herein in an individual comprising treating the individual's blood extracorporeally (i.e., outside the body or ex vivo) with a composition comprising a molecule under conditions that permit the molecule to function to modulate immune response, and returning the blood to the individual.

Unit Dosages, Articles of Manufacture, and Kits

Also provided are unit dosage forms of compositions, each dosage containing from about 0.01 mg to about 50 mg, including for example any of about 0.1 mg to about 50 mg, about 1 mg to about 50 mg, about 5 mg to about 40 mg, about 10 mg to about 20 mg, or about 15 mg of the molecule. In some embodiments, the unit dosage forms of molecule composition comprises about any of 0.01 mg-0.1 mg, 0.1 mg-0.2 mg, 0.2 mg-0.25 mg, 0.25 mg-0.3 mg, 0.3 mg-0.35 mg, 0.35 mg-0.4 mg, 0.4 mg-0.5 mg, 0.5 mg-1.0 mg, 10 mg-20 mg, 20 mg-50 mg, 50 mg-80 mg, 80 mg-100 mg, 100 mg-150 mg, 150 mg-200 mg, 200 mg-250 mg, 250 mg-300 mg, 300 mg-400 mg, or 400 mg-500 mg molecule. In some embodiments, the unit dosage form comprises about 0.25 mg molecule. The term "unit dosage form" refers to a physically discrete unit suitable as unitary dosages for an individual, each unit containing a predetermined quantity of active material calculated to produce the desired therapeutic effect, in association with a suitable pharmaceutical carrier, diluent, or excipient. These unit dosage forms can be stored in a suitable packaging in single or multiple unit dosages and may also be further sterilized and sealed.

Also provided are articles of manufacture comprising the compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions (or unit dosages forms and/or articles of manufacture) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

The compositions and formulations of the present invention are useful for the treatment of conditions associated with modulation of immune response.

Veterinary Use

In addition to the above, the present invention further provides methods and materials useful for veterinary indications, including the treatment of non-human mammals for immune disorders and diseases. In particular embodiments, the methods and materials of the present invention that are useful for veterinary uses comprise peptide domains originating from the same species as the veterinary host/patient. The non-human mammal may be suffering from any immune disorder or disease, including autoimmune hemolytic anemia (AIHA), immune thrombocytopenia purpura (ITP), rheumatoid arthritis or reactive arthritis. While the non-human mammal may be of any species, it is known that certain breeds of dogs are particularly susceptible to autoimmune disorders. For example, for the treatment of dogs, one or more Fc peptide domains and an oligomerization peptide domain, each of which is canine in origin, can be used. Dogs, particularly, are known to be susceptible to immune disorders, such as autoimmune hemolytic anemia (AIHA), in which the dog's own immune system binds to and destroys the dog's red blood cells. In dogs with AIHA or immune thrombocytopenia purpura (ITP) that do not respond to conventional therapies, or in severe ITP where the risk of fatal hemorrhage is considered substantial IVIG of human origin has been utilized for treatment. See for example, Kellerman et al. (1997) J Vet Int Med, 11:327-332. However, dogs treated with human IVIG consistently generate dog-anti-human-antibody (DAHA), which can trigger anaphylaxis upon repeated use of the human IVIG. For this reason, treatment of veterinary patients with the presently available IVIG compositions is severely limited. Thus, the methods and materials of the present invention provide rIVIG compositions of canine origin, and methods of treatment of dogs exhibiting canine immune disorders, such as AIHA and ITP.

In veterinary indications, the present invention comprises rIVIG polypeptides comprising peptide domains originating from the same species as the veterinary host/patient. Thus for the treatment of dogs, the present invention comprises rIVIG polypeptides comprising one or more canine Fc peptide domains and a canine oligomerization peptide domain. As in human treatment, preferred embodiments of the invention comprise two or more Fc portions joined by a flexible linker in order to allow intramolecular interaction, and a trimerizing peptide domain. The rIVIG polypeptides comprising an oligomerization peptide domain of canine origin may be useful for the treatment of dogs exhibiting canine immune disorders.

Recombinant Immunoglobulin Fusion Proteins

P7005H is a fusion protein consisting of a human Fc portion, comprising the human IgG1 heavy chain CH2 and CH3 regions, and the extracellular domain (ECD) of human CD40L. The human Fc portion can dimerize, and the CD40L ECD, trimerize. Hence, it is expected that the fusion protein will form hexamers containing three dimeric Fc and two trimeric CD40L. The mature P7005H contains three dimeric Fc portions comprising human IgG1 heavy chain CH2 and CH3 regions, and is expected to exhibit excellent IVIG-mimetic activity. However, because each functional Fc domain is on a separate peptide chain, the formation of dimeric Fc's is not homogeneous. Moreover, disulfide linkages between the expressed peptide chains can vary significantly, and intermolecular interactions can occur as well as intramolecular, leading to 'zippered' oligomers that are much larger than hexamers. Accordingly, the composition formed by P7005H is significantly less homogeneous than desired, and includes aggregated proteins that are not properly folder and hence will not be active. Accordingly, in order for the protein compositions containing P7005H to be more acceptable, further purification steps are needed in order to isolate the hexamers that are expected to be most active. The need for such purification makes the P7005H less commercially viable because preparation of a homogeneous composition would require further purification steps.

In order to address the issues of homogeneity of rIVIG compositions of the present invention, the inventors developed a series of single chain human Fc fusion peptides.

P8001Z is a fusion protein comprising a single chain human Fc, comprising two tandem human CH2-CH3Fc domains, each CH2-CH3 Fc domain comprising the human IgG1 heavy chain CH2 and CH3 regions, and the GXY triplet repeats and NC1 domain derived from human collagen 21. The single chain Fc peptide includes a flexible linker (GGGGS)$_5$, between the two CH2-CH3 Fc domains, which allows the thermodynamically favored intramolecular interaction and promotes the formation of a functional Fc peptide in a single chain. This intramolecular interaction is expected to minimize the formation of intermolecular disulfide linkages and maximize the formation of single species of functional single chain Fc peptides. The GXY triplet repeats are responsible for trimerization of collagen, and are expected to bring together three Fc regions, in each of which the two tandem CH2-CH3 Fc domains connected by a flexible linker may interact. The product of P8001Z is therefore expected to be more homogeneous than that of the P7005H construct.

P8003Z is a fusion protein comprising a single chain human IgG kappa or light chain constant region (CL), a first Fc domain comprising an entire IgG constant region (CH1, CH2, and CH3) with a second Fc domain (comprising CH2 and CH3), connected in tandem to the C-terminus of the first Fc region through a flexible linker, which is preferably a (G4S)$_5$ linker. The flexible linker allows the construct to assume conformations in which the first and second Fc domains may interact intramolecularly. The C-terminus of the second Fc domain is connected in tandem to the collagen GXY triplet repeat and NC1 domain (a trimerization domain) Similar to P8001Z, the collagen GXY repeats and the NC1 domain exhibit an intrinsic trimerizing activity to bring three single chains Fc peptides together, each comprising a first CH2-CH3 Fc domain connected to a second CH2-CH3 Fc domain through a flexible linker, in a conformation in which the first and second CH2-CH3 Fc domains may interact. It should also be mentioned that the CL domain heterodimerizes with the CH1 domain. The CL/CH1 domain plays a role in scavenging complement components, which may further lessen the complement immune response that is present in many autoimmune disorders.

P8020Z is a fusion protein consisting of an N-terminal portion human mannose binding protein (MBP) and a single chain Fc peptide similar to that of the P8003Z, comprising, in order from N to C-terminal direction, CL-CH1-CH2-CH3-flexible linker-CH2-CH3. The N-terminal portion of human MBP has an intrinsic trimerizing capacity and is responsible for oligomerization of the fusion protein. In contrast to the design of P8003Z, the oligomerization domain of P8020Z is located at the N-terminus of the fusion protein and the Ig Fc region is located at the C-terminus, as found in native immunoglobulin molecules. The structure of P8020Z, having the single chain Fc peptides located at the C-terminal end of the fusion protein is expected to closely mimic the orientation of a regular antibody for its interaction with Fc receptors.

The above recombinant rIVIG constructs have been made and expressed in 293T cells, and the produced proteins can be purified using purification techniques that are known in the art.

To determine if the rIVIG proteins have folded properly, such that they comprise predominantly hexameric Fc structure, the purified proteins are analysed by size exclusion chromatographic (SEC) profiling. FIG. 2 shows the SEC profiles of each protein product.

The FcγR binding activities of these rIVIG protein were analysed and compared with that of the purified monomeric human IgG1 antibody (FIG. 3).

The P8003Z and P8020Z constructs were also tested for their therapeutic effects using a mouse collagen-induced arthritis model.

Mice were primed with bovine type II collagen with complete Freund adjuvant (CFA) and boosted with the same collagen with incomplete Freund Adjuvant (IFA) on day 21. P8020Z was administered intraperitoneally on Day 18. The inflamed paws were scored from day 26 on. FIG. 4 shows mice treated with P8020 showed a much attenuated inflammation than the control mice treated with PBS.

Although the following examples illustrate the practice of the present invention in various embodiments, the examples should not be construed as limiting the scope of the invention. Other embodiments will be apparent to one of skill in the art from consideration of the specifications and examples.

EXAMPLES

Example 1

Construction of P7005H

The P7005H protein is expressed from a mammalian expression plasmid pMEhFcN1-7005, which encodes a protein of 395 amino acids under the control of cytomegalovirus (CMV) immediately early gene promoter. From the N-terminus, the encoded product consists of the human IgG1 hinge, CH2, and CH3 regions joined to the extracellular domain of human CD40L. The following is the coding sequence of the mature protein product (375 amino acids) as generated from the production system (SEQUENCE ID NO: 1).

Protein sequence of P7005H (375 amino acids) (SEQUENCE ID NO: 1):

```
  1    DKTHTCPPCP APELLGGPSV FLFPPKPKDT LMISRTPEVT CVVVDVSHED

51    PEVKFNWYVD GVEVHNAKTK PREEQYNSTY RVVSVLTVLH QDWLNGKEYK

101    CKVSNKALPA PIEKTISKAK GQPREPQVYT LPPSRDELTK NQVSLTCLVK

151    GFYPSDIAVE WESNGQPENN YKTTPPVLDS DGSFFLYSKL TVDKSRWQQG

201    NVFSCSVMHE ALHNHYTQKS LSLSPGGILG DQNPQIAAHV ISEASSKTTS

251    VLQWAEKGYY TMSNNLVTLE NGKQLTVKRQ GLYYIYAQVT FCSNREASSQ

301    APFIASLCLK SPGRFERILL RAANTHSSAK PCGQQSIHLG GVFELQPGAS

351    VFVNVTDPSQ VSHGTGFTSF GLLKL
```

TABLE 2

| P7005H Protein domains: | Amino Acid Numbers (SEQ ID NO: 1) |
|---|---|
| human IgG1 hinge, CH2, and CH3 regions | 1-226 |
| GIL, cloning site | 227-229 |
| human CD40L trimerization domain | 230-375 |

TABLE 3

| P8001Z Protein domains: | Amino Acid Numbers (SEQ ID NO: 2) |
|---|---|
| human IgG1 CH2 and CH3 regions | 1-216 |
| (G4S)5 | 217-241 |
| human IgG1 CH2 and CH3 regions | 242-457 |
| G4S | 458-462 |
| GXY)11-NC1 | 463-519 |

Example 2

Construction of P8001Z

The P8001Z protein is expressed from a mammalian expression plasmid pHCM-rIVIG V1, which encodes a protein of 539 amino acids under the control of cytomegalovirus (CMV) immediately early gene promoter. From the N-terminus, the encoded product consists of a first CH2-CH3 Fc domain comprising human IgG1 heavy chain CH2 and CH3 regions; followed by a flexible linker comprising five repeats of G4S linkers (GGGGS)5; followed by a second CH2-CH3 Fc domain comprising human IgG1 heavy chain CH2 and CH3 regions; followed by eleven copies of GXY triplets and NC1 domain from human Collagen 21 A1 ((GXY)11-NC1). The following is the coding sequence of the mature protein product (519 amino acids) as generated from the production system (SEQUENCE ID NO: 2).

Protein sequence of P8001Z (519 amino acids) (SEQUENCE ID NO: 2):

Example 3

Construction of P8002Z

The P8002Z protein is expressed from a mammalian expression plasmid pHCM-rIVIG V2, which encodes a protein of 529 amino acids under the control of cytomegalovirus (CMV) immediately early gene promoter. From the N-terminus, the encoded product consists of a first CH2-CH3 Fc domain comprising human IgG1 heavy chain CH2 and CH3 regions; followed by three repeats of G4S linkers (GGGGS)3; followed by a second CH2-CH3 Fc domain comprised of human IgG1 heavy chain CH2 and CH3 regions; followed by a GGGGS linker; followed by eleven copies of GXY triplets and NC1 domain from human Collagen 21 A1 ((GXY)11-NC1). The following is the coding sequence of the mature protein product (509 amino acids) as generated from the production system (SEQUENCE ID NO: 3).

```
  1    APELLGGPSV FLFPPKPKDT LMISRTPEVT CVVVDVSHED PEVKFNWYVD

51    GVEVHNAKTK PREEQYNSTY RVVSVLTVLH QDWLNGKEYK CKVSNKALPA

101    PIEKTISKAK GQPREPQVYT LPPSRDELTK NQVSLTCLVK GFYPSDIAVE

151    WESNGQPENN YKTTPPVLDS DGSFFLYSKL TVDKSRWQQG NVFSCSVMHE

201    ALHNHYTQKS LSLSPGGGGG SGGGGSGGGG SGGGGSGGGG SAPELLGGPS

251    VFLFPPKPKD TLMISRTPEV TCVVVDVSHE DPEVKFNWYV DGVEVHNAKT

301    KPREEQYNST YRVVSVLTVL HQDWLNGKEY KCKVSNKALP APIEKTISKA

351    KGQPREPQVY TLPPSRDELT KNQVSLTCLV KGFYPSDIAV EWESNGQPEN

401    NYKTTPPVLD SDGSFFLYSK LTVDKSRWQQ GNVFSCSVMH EALHNHYTQK

451    SLSLSPGGGG GSGPPGISGP PGDPGLPGKD GDHGKPGIQG QPGPPGICDP

501    SLCFSVIARR DPFRKGPNY
```

```
Protein sequence of P8002Z (509 amino acids) (SEQUENCE ID NO: 3):
  1    APELLGGPSV FLFPPKPKDT LMISRTPEVT CVVVDVSHED PEVKFNWYVD

51    GVEVHNAKTK PREEQYNSTY RVVSVLTVLH QDWLNGKEYK CKVSNKALPA

101    PIEKTISKAK GQPREPQVYT LPPSRDELTK NQVSLTCLVK GFYPSDIAVE

151    WESNGQPENN YKTTPPVLDS DGSFFLYSKL TVDKSRWQQG NVFSCSVMHE

201    ALHNHYTQKS LSLSPGGGGG SGGGGSGGGG SAPELLGGPS VFLFPPKPKD

251    TLMISRTPEV TCVVVDVSHE DPEVKFNWYV DGVEVHNAKT KPREEQYNST

301    YRVVSVLTVL HQDWLNGKEY KCKVSNKALP APIEKTISKA KGQPREPQVY

351    TLPPSRDELT KNQVSLTCLV KGFYPSDIAV EWESNGQPEN NYKTTPPVLD

401    SDGSFFLYSK LTVDKSRWQQ GNVFSCSVMH EALHNHYTQK SLSLSPGGGG

451    GSGPPGISGP PGDPGLPGKD GDHGKPGIQG QPGPPGICDP SLCFSVIARR

501    DPFRKGPNY
```

TABLE 4

| P8002Z Protein domains: | Amino Acid Numbers (SEQ ID NO: 3) |
|---|---|
| human IgG1 CH2 and CH3 regions | 1-216 |
| (G4S)₃ | 217-231 |
| human IgG1 CH2 and CH3 regions | 232-447 |
| G4S | 448-452 |
| ((GXY)11-NC1) | 453-509 |

Example 4

Construction of P8003Z

The P8003Z protein is expressed from a mammalian expression plasmid pHCM-rIVIG V3, which encodes a protein of 788 amino acids under the control of cytomegalovirus (CMV) immediately early gene promoter. From the N-terminus, the encoded product consists of the human kappa light chain constant region (CL); followed by two repeats of G4S linkers (G4S)$_2$; followed by a CH1-hinge-CH2-CH3 Fc domain comprising human IgG1 heavy chain constant region (CH1-hinge-CH2-CH3); followed by a flexible linker comprising five repeats of G4S linkers (GGGGS)$_5$; followed by a hinge-CH2-CH3 Fc domain comprising human IgG1 heavy chain hinge, CH2 and CH3 regions; followed by eleven copies of GXY triplets and NC1 domain from human Collagen 21 A1 ((GXY)11-NC1). The following is the sequence of the mature protein product (768 amino acids) as generated from the production system (SEQUENCE ID NO: 4).

```
Protein sequence of P8003Z (768 amino acids)(SEQUENCE ID NO: 4):
  1    VEIKRTVAAP SVFIFPPSDE QLKSGTASVV CLLNNFYPRE AKVQWKVDNA

51    LQSGNSQESV TEQDSKDSTY SLSSTLTLSK ADYEKHKVYA CEVTHQGLSS

101    PVTKSFNRGE CGGGGSGGGG SASTKGPSVF PLAPSSKSTS GGTAALGCLV

151    KDYFPEPVTV SWNSGALTSG VHTFPAVLQS SGLYSLSSVV TVPSSSLGTQ

201    TYICNVNHKP SNTKVDKRVE PKSCDKTHTC PPCPAPELLG GPSVFLFPPK

251    PKDTLMISRT PEVTCVVVDV SHEDPEVKFN WYVDGVEVHN AKTKPREEQY

301    NSTYRVVSVL TVLHQDWLNG KEYKCKVSNK ALPAPIEKTI SKAKGQPREP

351    QVYTLPPSRD ELTKNQVSLT CLVKGFYPSD IAVEWESNGQ PENNYKTTPP

401    VLDSDGSFFL YSKLTVDKSR WQQGNVFSCS VMHEALHNHY TQKSLSLSPG

451    GGGSGGGGS GGGGSGGGGS GGGGSEPKSC DKTHTCPPCP APELLGGPSV

501    FLFPPKPKDT LMISRTPEVT CVVVDVSHED PEVKFNWYVD GVEVHNAKTK

551    PREEQYNSTY RVVSVLTVLH QDWLNGKEYK CKVSNKALPA PIEKTISKAK

601    GQPREPQVYT LPPSRDELTK NQVSLTCLVK GFYPSDIAVE WESNGQPENN

651    YKTTPPVLDS DGSFFLYSKL TVDKSRWQQG NVFSCSVMHE ALHNHYTQKS

701    LSLSPGGGGG SGPPGISGPP GDPGLPGKDG DHGKPGIQGQ PGPPGICDPS

751    LCFSVIARRD PFRKGPNY
```

TABLE 5

| P8003Z Protein domains: | Amino Acid Numbers (SEQ ID NO: 4) |
|---|---|
| Human kappa chain constant region | 1-111 |
| (G4S)$_2$ | 112-121 |
| human IgG1 CH1, hinge, CH2 and CH3 regions | 122-450 |
| (G4S)$_5$ | 451-475 |
| human IgG1 hinge, CH2 and CH3 | 476-706 |
| G4S | 707-711 |
| (GXY)11-NC1 | 712-768 |

Example 5

Construction of P8004Z

The P8004Z protein is expressed from a mammalian expression plasmid pHCM-rIVIG V4, which encodes a protein of 569 amino acids under the control of cytomegalovirus (CMV) immediately early gene promoter. From the N-terminus, the encoded product consists of a first hinge-CH2-CH3 Fc domain comprising human IgG1 heavy chain hinge, CH2 and CH3 regions (hinge-CH2-CH3); followed by a flexible linker (GGGGS)$_5$; followed by a second hinge-CH2-CH3 Fc domain comprising human IgG1 heavy chain hinge, CH2 and CH3 regions; followed by eleven copies of GXY triplets and NC1 domain from human Collagen 21 A1 (GXY11-NC1). The following is the coding sequence of the mature protein product (549 amino acids) as generated from the production system (SEQUENCE ID NO: 5).

```
Protein sequence of P8004Z (549 amino acids)(SEQUENCE ID NO: 5):
  1 EPKSCDKTHT CPPCPAPELL GGPSVFLFPP KPKDTLMISR TPEVTCVVVD

51 VSHEDPEVKF NWYVDGVEVH NAKTKPREEQ YNSTYRVVSV LTVLHQDWLN

101 GKEYKCKVSN KALPAPIEKT ISKAKGQPRE PQVYTLPPSR DELTKNQVSL

151 TCLVKGFYPS DIAVEWESNG QPENNYKTTP PVLDSDGSFF LYSKLTVDKS

201 RWQQGNVFSC SVMHEALHNH YTQKSLSLSP GGGGSGGGG SGGGGSGGGG

251 SGGGGSEPKS CDKTHTCPPC PAPELLGGPS VFLFPPKPKD TLMISRTPEV

301 TCVVVDVSHE DPEVKFNWYV DGVEVHNAKT KPREEQYNST YRVVSVLTVL

351 HQDWLNGKEY KCKVSNKALP APIEKTISKA KGQPREPQVY TLPPSRDELT

401 KNQVSLTCLV KGFYPSDIAV EWESNGQPEN NYKTTPPVLD SDGSFFLYSK

451 LTVDKSRWQQ GNVFSCSVMH EALHNHYTQK SLSLSPGGGG GSGPPGISGP

501 PGDPGLPGKD GDHGKPGIQG QPGPPGICDP SLCFSVIARR DPFRKGPNY
```

TABLE 6

| P8004Z Protein domains: | Amino Acid Numbers (SEQ ID NO: 5) |
|---|---|
| human IgG1 hinge, CH2 and CH3 regions | 1-231 |
| (G4S)$_5$ | 232-256 |
| human IgG1 hinge, CH2 and CH3 regions | 257-487 |
| G4S | 488-492 |
| (GXY)11-NC1 | 493-549 |

Example 6

Construction of P8020Z

The P8020Z protein is expressed from a mammalian expression plasmid pHCM-rIVIG V20, which encodes a protein of 816 amino acids under the control of cytomegalovirus (CMV) immediately early gene promoter. From the N-terminus, the encoded product consists of the human mannose-binding protein (hMBP) N-terminal peptide-hMBP collagen triple helix domain; followed by three repeats of G4S linkers (GGGGS)$_3$; followed by human kappa light chain constant region (CL); followed by two repeats of G4S linkers (G4S)$_2$; followed by a first CH1-hinge-CH2-CH3 Fc domain comprising human IgG1 heavy chain constant region (CH1-hinge-CH2-CH3); followed by a flexible linker comprising five repeats of GGGGS linkers (GGGGS)$_5$; followed by a hinge-CH2-CH3 Fc domain comprising human IgG1 heavy chain hinge, CH2 and CH3 regions. The following is the sequence of the mature protein product (796 amino acids) as generated from the production system: Protein sequence of P8020Z (796 amino acids) (SEQUENCE ID NO: 6):

```
  1  ETVTCEDAQK TCPAVIACSS PGINGFPGKD GRDGTKGEKG EPGQGLRGLQ

51  GPPGKLGPPG NPGPSGSPGP KGQKGDPGKG GGGSGGGGSG GGGSRTVAAP

101  SVFIFPPSDE QLKSGTASVV CLLNNFYPRE AKVQWKVDNA LQSGNSQESV

151  TEQDSKDSTY SLSSTLTLSK ADYEKHKVYA CEVTHQGLSS PVTKSFNRGE

201  CGGGGSGGGG SASTKGPSVF PLAPSSKSTS GGTAALGCLV KDYFPEPVTV

251  SWNSGALTSG VHTFPAVLQS SGLYSLSSVV TVPSSSLGTQ TYICNVNHKP

301  SNTKVDKRVE PKSCDKTHTC PPCPAPELLG GPSVFLFPPK PKDTLMISRT

351  PEVTCVVVDV SHEDPEVKFN WYVDGVEVHN AKTKPREEQY NSTYRVVSVL

401  TVLHQDWLNG KEYKCKVSNK ALPAPIEKTI SKAKGQPREP QVYTLPPSRD

451  ELTKNQVSLT CLVKGFYPSD IAVEWESNGQ PENNYKTTPP VLDSDGSFFL

501  YSKLTVDKSR WQQGNVFSCS VMHEALHNHY TQKSLSLSPG GGGGSGGGGS

551  GGGGSGGGGS GGGGSEPKSC DKTHTCPPCP APELLGGPSV FLFPPKPKDT

601  LMISRTPEVT CVVVDVSHED PEVKFNWYVD GVEVHNAKTK PREEQYNSTY

651  RVVSVLTVLH QDWLNGKEYK CKVSNKALPA PIEKTISKAK GQPREPQVYT

701  LPPSRDELTK NQVSLTCLVK GFYPSDIAVE WESNGQPENN YKTTPPVLDS

751  DGSFFLYSKL TVDKSRWQQG NVFSCSVMHE ALHNHYTQKS LSLSPG
```

TABLE 7

| P8020Z Protein domains: | Amino Acid Numbers (SEQ ID NO: 6) |
|---|---|
| human mannose-binding protein (MBP) trimerization domain | 1-79 |
| (G4S)3 | 80-94 |
| human kappa constant region (CL) | 95-201 |
| (G4S)2 | 202-211 |
| human IgG1 CH1, hinge, CH2, and CH3 regions | 212-540 |
| (G4S)5 | 541-565 |
| human IgG1 hinge, CH2, and CH3 regions | 566-796 |

Example 7

Construction of K8020Z

The K8020Z protein is expressed from a mammalian expression plasmid pHCM-rIVIG V40, which encodes a protein of 822 amino acids under the control of cytomegalovirus (CMV) immediately early gene promoter. From the N-terminus, the encoded product consists of the canine mannose-binding protein (MBP) N-terminal peptide-canine MBP collagen triple helix domain; followed by three repeats of G4S linkers (GGGGS)3; followed by canine kappa light chain constant region (CL); followed by two repeats of G4S linkers (GGGGS)2; followed by a canine CH1-hinge-CH2-CH3 Fc domain comprising IgG subclass B heavy chain constant region (CH1-hinge-CH2-CH3); followed by a flexible linker comprising five repeats of G4S (GGGGS)5; followed by a canine hinge-CH2-CH3 Fc domain comprising canine IgG subclass B heavy chain hinge, CH2, and CH3 regions. The following is the coding sequence of the mature protein product (802 amino acids) as generated from the production system (SEQUENCE ID NO: 7).

```
Protein sequence of K8020Z (802 amino acids) (SEQUENCE ID NO: 7):
  1  DKEALSEAQR TCPVVTCALP GRDGRDGLKG EKGEPGQGLR GLQGPPGKVG

51  PPGNTGAPGA PGLKGHKGDR GDGGGGSGGG GSGGGGSRND AQPAVYLFQP

101  SPDQLHTGSA SVVCLLNSFY PKDINVKWKV DGVIQDTGIQ ESVTEQDKDS

151  TYSLSSTLTM SSTEYLSHEL YSCEITHKSL PSTLIKSFQR SECQRVDGGG

201  GSGGGGSAST TAPSVFPLAP SCGSTSGSTV ALACLVSGYF PEPVTVSWNS

251  GSLTSGVHTF PSVLQSSGLY SLSSMVTVPS SRWPSETFTC NVAHPASKTK

301  VDKPVPKREN GRVPRPPDCP KCPAPEMLGG PSVFIFPPKP KDTLLIARTP

351  EVTCVVVDLD PEDPEVQISW FVDGKQMQTA KTQPREEQFN GTYRVVSVLP

401  IGHQDWLKGK QFTCKVNNKA LPSPIERTIS KARGQAHQPS VYVLPPSREE

451  LSKNTVSLTC LIKDFFPPDI DVEWQSNGQQ EPESKYRTTP PQLDEDGSYF

501  LYSKLSVDKS RWQRGDTFIC AVMHEALHNH YTQKSLSHSP GGGGGSGGGG
```

```
551  SGGGGSGGGG SGGGGSPKRE NGRVPRPPDC PKCPAPEMLG GPSVFIFPPK

601  PKDTLLIART PEVTCVVVDL DPEDPEVQIS WFVDGKQMQT AKTQPREEQF

651  NGTYRVVSVL PIGHQDWLKG KQFTCKVNNK ALPSPIERTI SKARGQAHQP

701  SVYVLPPSRE ELSKNTVSLT CLIKDFFPPD IDVEWQSNGQ QEPESKYRTT

751  PPQLDEDGSY FLYSKLSVDK SRWQRGDTFI CAVMHEALHN HYTQKSLSHS

801  PG
```

TABLE 8

| K8020Z Protein domains: | Amino Acid Numbers (SEQ ID NO: 7) |
|---|---|
| Canine MBP trimerization domain | 1-72 |
| (G4S)₃ | 73-87 |
| canine kappa chain constant region (CL) | 88-197 |
| (G4S)₂ | 198-207 |
| canine IgG-B CH1, hinge, CH2, and CH3 regions | 208-541 |
| (G4S)₅ | 542-566 |
| canine IgG-B hinge, CH2, and CH3 regions | 567-802 |

B heavy chain constant region (CH1-hinge-CH2-CH3); followed by a flexible linker comprising five repeats of G4S (GGGGS)₅; followed by a canine hinge-CH2-CH3 Fc domain comprising canine IgG subclass B heavy chain hinge, CH2, and CH3 regions; followed by eleven copies of GXY triplets and NC1 domain from canine Collagen 21 A1 ((GXY)11-NC1). The following is the sequence of the mature protein product (779 amino acids) as generated from the production system (SEQUENCE ID NO: 8).

```
Protein sequence of K8003Z (779 amino acids) (SEQUENCE ID NO: 8):
  1  RNDAQPAVYL FQPSPDQLHT GSASVVCLLN SFYPKDINVK WKVDGVIQDT

51  GIQESVTEQD KDSTYSLSST LTMSSTEYLS HELYSCEITH KSLPSTLIKS

101  FQRSECQRVD GGGGSGGGGS ASTTAPSVFP LAPSCGSTSG STVALACLVS

151  GYFPEPVTVS WNSGSLTSGV HTFPSVLQSS GLYSLSSMVT VPSSRWPSET

201  FTCNVAHPAS KTKVDKPVPK RENGRVPRPP DCPKCPAPEM LGGPSVFIFP

251  PKPKDTLLIA RTPEVTCVVV DLDPEDPEVQ ISWFVDGKQM QTAKTQPREE

301  QFNGTYRVVS VLPIGHQDWL KGKQFTCKVN NKALPSPIER TISKARGQAH

351  QPSVYVLPPS REELSKNTVS LTCLIKDFFP PDIDVEWQSN GQQEPESKYR

401  TTPPQLDEDG SYFLYSKLSV DKSRWQRGDT FICAVMHEAL HNHYTQKSLS

451  HSPGGGGSG GGGSGGGGSG GGGSGGGGSP KRENGRVPRP PDCPKCPAPE

501  MLGGPSVFIF PPKPKDTLLI ARTPEVTCVV VDLDPEDPEV QISWFVDGKQ

551  MQTAKTQPRE EQFNGTYRVV SVLPIGHQDW LKGKQFTCKV NNKALPSPIE

601  RTISKARGQA HQPSVYVLPP SREELSKNTV SLTCLIKDFF PPDIDVEWQS

651  NGQQEPESKY RTTPPQLDED GSYFLYSKLS VDKSRWQRGD TFICAVMHEA

701  LHNHYTQKSL SHSPGGGGGS GPPGISKEGP PGDPGLPGKD GDHGKPGIQG

751  QPGPPGICDP SLCFSVIVGR DPFRKGPNY
```

Example 8

Construction of K8003Z

The K8003Z protein is expressed from a mammalian expression plasmid pHCM-rIVIG V42, which encodes a protein of 779 amino acids under the control of cytomegalovirus (CMV) immediately early gene promoter. From the N-terminus, the encoded product consists of the canine kappa light chain constant region (CL); followed by two repeats of G4S linkers (GGGGS)₂; followed by a canine CH1-hinge-CH2-CH3 Fc domain comprising IgG subclass

TABLE 9

| K8003Z Protein domains: | Amino Acid Numbers (SEQ ID NO: 8) |
|---|---|
| Canine kappa chain constant region | 1-110 |
| (G4S)₂ | 111-120 |
| canine IgG-B CH1, hinge, CH2 and CH3 regions | 121-454 |
| (G4S)₅ | 455-479 |
| canine IgG-B hinge, CH2 and CH3 regions | 480-715 |
| G4S | 716-720 |
| canine Collagen 21 A1 (GXY)11-NC1 | 721-779 |

REFERENCES

1. Behring and Kitasato (1890) uber das Zustandekommen der Diphtherie-Immunidat and der Tetanus-Immunitat bei Thieren. Dtsch med Wochenschr 16:1113-1114
2. Bruton (1952) Agaqmmaglobulinemia. Pediatrics 9:722-728.
3. Barandun et al. (1962) Intravenous administration of human gamma-globulin. Vox Sang. 7:157-174.
4. Schultze and Schwick (1962) On new possibilities of intravenous gamma globulin administration. Dtsch Med Wochenschr. 87:1643-1644
5. Kornhuber (1971) Intravenose g-Globulin-Therapie. Erfahrungen mit einer neuartigen Praparation. Mschr Kinderheilk 119:528-530.
6. Morell and Skvaril (1980) Structure and biological properties of immunoglobulins and gamma-globulin preparations. II. Properties of gamma-globulin preparations. Schweiz Med Wochenschr. 110(3):80-85.
7. Stephan (1975) Undegraded human immunoglobulin for intravenous use. Vox Sang. 28:422-437.
8. Hansi et al. (1980) Clinical results with a new intravenous immunoglobulin preparation. Dtsch Med Wochenschr. 105:1675-1680.
9. Luthardt (1980) Intravenous immunoglobulin administration for antibody deficiency. Dtsch Med Wochenschr. 105:993-997.
10. Nolte et al. (1979) Intravenous immunoglobulin therapy for antibody deficiency. Clin Exp Immunol. 36:237-243.
11. Imbach et al. (1981) Igh-dose intravenous gammaglobulin for idiopathic thrombocytopenic purpura in childhood. Lancet 317:1228-1231.
12. Noseworthy et al. (2000) IV immunoglobulin does not reverse established weakness in MS. Neurology. 55:1135-1143.
13. Fehr et al. (1982) Transient reversal of thrombocytopenia in idiopathic thrombocytopenic purpura by high-dose intravenous gamma globulin. N Engl J Med. 306:1254-1258.
14. Newland et al. (1983) High-dose intravenous IgG in adults with autoimmune thrombocytopenia. Lancet. 1:84-87.
15. Bussel and Hilgartner (1984) The use and mechanism of action of intravenous immunoglobulin in the treatment of immune haematologic disease. Br J Haematol. 56:1-7.
16. Debré et al. (1993) Infusion of Fc gamma fragments for treatment of children with acute immune thrombocytopenic purpura. Lancet. 342:945-949.
17. Samuelsson et al. (2001) Anti-inflammatory activity of IVIG mediated through the inhibitory Fc receptor. Science 291:484-486.
18. Teeling et al. (2001) Therapeutic efficacy of intravenous immunoglobulin preparations depends on the immunoglobulin G dimers: studies in experimental immune thrombocytopenia. Blood. 98:1095-1099.
19. Jain et al. (2012) Fully recombinant IgG2a Fc multimers (stradomers) effectively treat collagen-induced arthritis and prevent idiopathic thrombocytopenic purpura in mice. Arthritis Res Ther. 14:R192.
20. Huang et al. (2010) Dendritic cells modulate platelet activity in IVIg-mediated amelioration of ITP in mice. Blood. 116:5002-5009.
21. Gillis et al. (2014) Frontier Immunology 5:1-13
22. Bergeron et al. (2014) Comparative functional characterization of canine IgG subclasses. Vet. Immunol. Immunopathol. 157:31-41.
23. Anthony et al. (2012) Novel roles for the IgG Fc glycan. Ann N Y Acad Sci. 1253:170-80
24. Kaneko et al. (2006) Anti-inflammatory activity of immunoglobulin G resulting from Fc sialylation. Science 313:670-673
25. Arnold et al. (2007) The impact of glycosylation on the biological function and structure of human immunoglobulins. Annu Rev Immunol. 25:21-50
26. Yamane-Ohnuki et al. (2004) Establishment of FUT8 knockout Chinese hamster ovary cells: an ideal host cell line for producing completely defucosylated antibodies with enhanced antibody-dependent cellular cytotoxicity Biotechnol Bioeng. 87:614-622).
27. Fugslang (2003) Protein Expression and Purification 31:247-249.
28. Kim et al. (2011) J. Biotechnology 151:319-324.
29. Lai et al. (2013) Pharmaceuticals 6:579-603

---

What is claimed:

1. A recombinant intravenous immunoglobulin (rIVIG) polypeptide comprising (a) a CL domain, a CH1 domain, and a single chain Fc peptide comprising two CH2-CH3 Fc domains; and (b) an oligomerization peptide domain, wherein the oligomerization peptide domain includes a collagen trimerization domain and the C-terminal end of the CL domain is linked to the N-terminal end of the CH1 domain by a short linker sequence.

2. The rIVIG polypeptide of claim 1, wherein the two CH2-CH3 Fc domains are joined via a flexible linker.

3. The rIVIG polypeptide of claim 2, wherein the flexible linker comprises from two to six repeats of the amino acid sequence G-G-G-G-S (SEQ ID NO: 9).

4. The rIVIG polypeptide of claim 2, wherein the flexible linker comprises five repeats of the amino acid sequence G-G-G-G-S (SEQ ID NO: 9).

5. The rIVIG polypeptide of claim 4, wherein the C-terminus of the oligomerization peptide domain is linked to the N-terminus of the CL domain.

6. The rIVIG polypeptide of claim 5, wherein the oligomerization peptide domain comprises amino acid nos. 1 to 79 of SEQ ID NO: 6.

7. The rIVIG polypeptide of claim 4, wherein the N-terminus of the oligomerization peptide domain is linked to the C-terminus of the single chain Fc peptide.

8. The rIVIG polypeptide of claim 7, wherein the oligomerization peptide domain comprises amino acid nos. 712 to 768 of SEQ ID NO: 4.

9. A composition for treatment of immune disorders comprising the rIVIG polypeptide of claim 1.

10. The composition of claim 9, wherein the rIVIG polypeptide comprises Fc regions of an isotype selected from the group consisting of IgG1, IgG2, IgG3, and IgG4.

11. The composition of claim 9, wherein the rIVIG polypeptide is predominantly afucosylated.

12. A method of treating a patient suffering from an autoimmune disorder, said method comprising administering to said patient an effective amount of a composition comprising the rIVIG polypeptide of claim 1.

13. A method of reducing the immune rejection response of a patient who has received an organ transplant, said method comprising administering to said patient an effective amount of a composition comprising recombinant immunoglobulin (rIVIG) protein, wherein said rIVIG protein comprises a CL domain, a CH1 domain, a single chain Fc peptide comprising two CH2-CH3 Fc domains, and an oligomerization peptide domain, wherein the oligomerization peptide domain includes a collagen trimerization domain and the C-terminal end of the CL domain is linked to the N-terminal end of the CH1 domain by a short linker sequence.

14. The method of claim 12, wherein the rIVIG protein comprises an amino acid sequence selected from the group consisting of SEQ ID NO: 4 and SEQ ID NO: 6.

15. A method of treating a non-human mammal suffering from an autoimmune disorder, said method comprising administering to said non-human mammal an effective amount of a composition comprising the recombinant intravenous immunoglobulin (rIVIG) protein of claim 1, wherein said rIVIG protein comprises an amino acid sequence that has been derived from a non-human mammal of the same species.

16. The method of claim 13, wherein the rIVIG protein comprises an amino acid sequence selected from the group consisting of SEQ ID NO: 4 and SEQ ID NO: 6.

17. A recombinant intravenous immunoglobulin (rIVIG) polypeptide comprising (a) a CL domain, a CH1 domain, and a single chain Fc peptide comprising two CH2-CH3 Fc domains; and (b) a collagen derived peptide domain, wherein the collagen-derived peptide domain is a collagen trimerization domain and the C-terminal end of the CL domain is linked to the N-terminal end of the CH1 domain by a short linker sequence.

18. The rIVIG polypeptide of claim 17, wherein the collagen derived peptide domain comprises amino acid nos. 712 to 768 of SEQ ID NO: 4.

19. A recombinant intravenous immunoglobulin (rIVIG) polypeptide comprising (a) a single chain Fc peptide comprising two CH2-CH3 Fc domains; and (b) a mannose binding protein (MBP) derived peptide domain, wherein the MBP-derived peptide domain includes a collagen trimerization domain.

20. The rIVIG polypeptide of claim 19, wherein the MBP-derived peptide domain comprises amino acid nos. 1 to 79 of SEQ ID NO: 6.

* * * * *

SEQUENCE LISTING

```
<160> NUMBER OF SEQ ID NOS: 10

<210> SEQ ID NO 1
<211> LENGTH: 375
<212> TYPE: PRT
<213> ORGANISM: Artificial Sequence
<220> FEATURE:
<223> OTHER INFORMATION: Synthesized

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80
```

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Ile Leu Gly Asp Gln Asn Pro Gln Ile Ala Ala His Val
225                 230                 235                 240

Ile Ser Glu Ala Ser Ser Lys Thr Thr Ser Val Leu Gln Trp Ala Glu
                245                 250                 255

Lys Gly Tyr Tyr Thr Met Ser Asn Asn Leu Val Thr Leu Glu Asn Gly
            260                 265                 270

Lys Gln Leu Thr Val Lys Arg Gln Gly Leu Tyr Tyr Ile Tyr Ala Gln
        275                 280                 285

Val Thr Phe Cys Ser Asn Arg Glu Ala Ser Ser Gln Ala Pro Phe Ile
    290                 295                 300

Ala Ser Leu Cys Leu Lys Ser Pro Gly Arg Phe Glu Arg Ile Leu Leu
305                 310                 315                 320

Arg Ala Ala Asn Thr His Ser Ser Ala Lys Pro Cys Gly Gln Gln Ser
                325                 330                 335

Ile His Leu Gly Gly Val Phe Glu Leu Gln Pro Gly Ala Ser Val Phe
            340                 345                 350

Val Asn Val Thr Asp Pro Ser Gln Val Ser His Gly Thr Gly Phe Thr
        355                 360                 365

Ser Phe Gly Leu Leu Lys Leu
    370                 375

<210> SEQ ID NO 2
<211> LENGTH: 519
<212> TYPE: PRT
<213> ORGANISM: Artificial Sequence
<220> FEATURE:
<223> OTHER INFORMATION: Synthesized

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ser Gly Gly Gly
210                 215                 220

Gly Ser Gly Gly Gly Gly Ser Gly Gly Gly Gly Ser Gly Gly Gly Gly
225                 230                 235                 240

Ser Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Gly Gly Gly Ser Gly Pro
        450                 455                 460

Pro Gly Ile Ser Gly Pro Pro Gly Asp Pro Gly Leu Pro Gly Lys Asp
465                 470                 475                 480
```

```
Gly Asp His Gly Lys Pro Gly Ile Gln Gly Gln Pro Gly Pro Pro Gly
                485                 490                 495

Ile Cys Asp Pro Ser Leu Cys Phe Ser Val Ile Ala Arg Arg Asp Pro
            500                 505                 510

Phe Arg Lys Gly Pro Asn Tyr
        515

<210> SEQ ID NO 3
<211> LENGTH: 509
<212> TYPE: PRT
<213> ORGANISM: Artificial Sequence
<220> FEATURE:
<223> OTHER INFORMATION: Synthesized

<400> SEQUENCE: 3

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Ser Gly Gly Gly
    210                 215                 220

Gly Ser Gly Gly Gly Ser Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Pro Pro Gly Ile Ser Gly Pro Pro Gly Asp Pro
450                 455                 460

Gly Leu Pro Gly Lys Asp Gly Asp His Gly Lys Pro Gly Ile Gln Gly
465                 470                 475                 480

Gln Pro Gly Pro Pro Gly Ile Cys Asp Pro Ser Leu Cys Phe Ser Val
                485                 490                 495

Ile Ala Arg Arg Asp Pro Phe Arg Lys Gly Pro Asn Tyr
            500                 505

<210> SEQ ID NO 4
<211> LENGTH: 768
<212> TYPE: PRT
<213> ORGANISM: Artificial Sequence
<220> FEATURE:
<223> OTHER INFORMATION: Synthesized

<400> SEQUENCE: 4

Val Glu Ile Lys Arg Thr Val Ala Ala Pro Ser Val Phe Ile Phe Pro
1               5                   10                  15

Pro Ser Asp Glu Gln Leu Lys Ser Gly Thr Ala Ser Val Val Cys Leu
            20                  25                  30

Leu Asn Asn Phe Tyr Pro Arg Glu Ala Lys Val Gln Trp Lys Val Asp
        35                  40                  45

Asn Ala Leu Gln Ser Gly Asn Ser Gln Glu Ser Val Thr Glu Gln Asp
    50                  55                  60

Ser Lys Asp Ser Thr Tyr Ser Leu Ser Ser Thr Leu Thr Leu Ser Lys
65                  70                  75                  80

Ala Asp Tyr Glu Lys His Lys Val Tyr Ala Cys Glu Val Thr His Gln
                85                  90                  95

Gly Leu Ser Ser Pro Val Thr Lys Ser Phe Asn Arg Gly Glu Cys Gly
            100                 105                 110

Gly Gly Gly Ser Gly Gly Gly Gly Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Gly Ser Gly Gly Gly Gly
    450                 455                 460

Ser Gly Gly Gly Gly Ser Gly Gly Gly Ser Glu Pro Lys Ser Cys
465                 470                 475                 480

Asp Lys Thr His Thr Cys Pro Pro Cys Pro Ala Pro Glu Leu Leu Gly
                485                 490                 495

Gly Pro Ser Val Phe Leu Phe Pro Pro Lys Pro Lys Asp Thr Leu Met
            500                 505                 510

Ile Ser Arg Thr Pro Glu Val Thr Cys Val Val Val Asp Val Ser His
        515                 520                 525

Glu Asp Pro Glu Val Lys Phe Asn Trp Tyr Val Asp Gly Val Glu Val
    530                 535                 540

His Asn Ala Lys Thr Lys Pro Arg Glu Glu Gln Tyr Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Ala Leu Pro Ala Pro Ile
            580                 585                 590

Glu Lys Thr Ile Ser Lys Ala Lys Gly Gln Pro Arg Glu Pro Gln Val
```

```
            595                 600                 605
Tyr Thr Leu Pro Pro Ser Arg Asp Glu Leu Thr Lys Asn Gln Val Ser
    610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Lys Leu Thr Val
                660                 665                 670

Asp Lys Ser Arg Trp Gln Gln Gly Asn Val Phe Ser Cys Ser Val Met
            675                 680                 685

His Glu Ala Leu His Asn His Tyr Thr Gln Lys Ser Leu Ser Leu Ser
    690                 695                 700

Pro Gly Gly Gly Gly Ser Gly Pro Gly Ile Ser Gly Pro Pro
705                 710                 715                 720

Gly Asp Pro Gly Leu Pro Gly Lys Asp Gly Asp His Gly Lys Pro Gly
                725                 730                 735

Ile Gln Gly Gln Pro Gly Pro Pro Gly Ile Cys Asp Pro Ser Leu Cys
                740                 745                 750

Phe Ser Val Ile Ala Arg Arg Asp Pro Phe Arg Lys Gly Pro Asn Tyr
                755                 760                 765

<210> SEQ ID NO 5
<211> LENGTH: 549
<212> TYPE: PRT
<213> ORGANISM: Artificial Sequence
<220> FEATURE:
<223> OTHER INFORMATION: Synthesized

<400> SEQUENCE: 5

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
```

```
            195                 200                 205
Ser Cys Ser Val Met His Glu Ala Leu His Asn His Tyr Thr Gln Lys
210                 215                 220

Ser Leu Ser Leu Ser Pro Gly Gly Gly Gly Ser Gly Gly Gly Gly
225                 230                 235                 240

Ser Gly Gly Gly Gly Ser Gly Gly Gly Ser Gly Gly Gly Gly Ser
                245                 250                 255

Glu Pro Lys Ser Cys Asp Lys Thr His Thr Cys Pro Pro Cys Pro Ala
                260                 265                 270

Pro Glu Leu Leu Gly Gly Pro Ser Val Phe Leu Phe Pro Pro Lys Pro
                275                 280                 285

Lys Asp Thr Leu Met Ile Ser Arg Thr Pro Glu Val Thr Cys Val Val
                290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
                355                 360                 365

Leu Pro Ala Pro Ile Glu Lys Thr Ile Ser Lys Ala Lys Gly Gln Pro
                370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
                435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Gly Gly Gly Ser Gly Pro Pro Gly
                485                 490                 495

Ile Ser Gly Pro Pro Gly Asp Pro Gly Leu Pro Gly Lys Asp Gly
                500                 505                 510

His Gly Lys Pro Gly Ile Gln Gly Gln Pro Gly Pro Pro Gly Ile Cys
                515                 520                 525

Asp Pro Ser Leu Cys Phe Ser Val Ile Ala Arg Arg Asp Pro Phe Arg
                530                 535                 540

Lys Gly Pro Asn Tyr
545

<210> SEQ ID NO 6
<211> LENGTH: 796
<212> TYPE: PRT
<213> ORGANISM: Artificial Sequence
<220> FEATURE:
<223> OTHER INFORMATION: Synthesized

<400> SEQUENCE: 6

Glu Thr Val Thr Cys Glu Asp Ala Gln Lys Thr Cys Pro Ala Val Ile
```

-continued

```
1               5                   10                  15
Ala Cys Ser Ser Pro Gly Ile Asn Gly Phe Pro Gly Lys Asp Gly Arg
                20                  25                  30
Asp Gly Thr Lys Gly Glu Lys Gly Glu Pro Gly Gln Gly Leu Arg Gly
                35                  40                  45
Leu Gln Gly Pro Pro Gly Lys Leu Gly Pro Pro Gly Asn Pro Gly Pro
                50                  55                  60
Ser Gly Ser Pro Gly Pro Lys Gly Gln Lys Gly Asp Pro Gly Lys Gly
65                  70                  75                  80
Gly Gly Gly Ser Gly Gly Gly Ser Gly Gly Gly Ser Arg Thr
                85                  90                  95
Val Ala Ala Pro Ser Val Phe Ile Phe Pro Pro Ser Asp Glu Gln Leu
                100                 105                 110
Lys Ser Gly Thr Ala Ser Val Val Cys Leu Leu Asn Asn Phe Tyr Pro
                115                 120                 125
Arg Glu Ala Lys Val Gln Trp Lys Val Asp Asn Ala Leu Gln Ser Gly
                130                 135                 140
Asn Ser Gln Glu Ser Val Thr Glu Gln Asp Ser Lys Asp Ser Thr Tyr
145                 150                 155                 160
Ser Leu Ser Ser Thr Leu Thr Leu Ser Lys Ala Asp Tyr Glu Lys His
                165                 170                 175
Lys Val Tyr Ala Cys Glu Val Thr His Gln Gly Leu Ser Ser Pro Val
                180                 185                 190
Thr Lys Ser Phe Asn Arg Gly Glu Cys Gly Gly Gly Ser Gly Gly
                195                 200                 205
Gly Gly Ser Ala Ser Thr Lys Gly Pro Ser Val Phe Pro Leu Ala Pro
                210                 215                 220
Ser Ser Lys Ser Thr Ser Gly Gly Thr Ala Ala Leu Gly Cys Leu Val
225                 230                 235                 240
Lys Asp Tyr Phe Pro Glu Pro Val Thr Val Ser Trp Asn Ser Gly Ala
                245                 250                 255
Leu Thr Ser Gly Val His Thr Phe Pro Ala Val Leu Gln Ser Ser Gly
                260                 265                 270
Leu Tyr Ser Leu Ser Ser Val Val Thr Val Pro Ser Ser Ser Leu Gly
                275                 280                 285
Thr Gln Thr Tyr Ile Cys Asn Val Asn His Lys Pro Ser Asn Thr Lys
                290                 295                 300
Val Asp Lys Arg Val Glu Pro Lys Ser Cys Asp Lys Thr His Thr Cys
305                 310                 315                 320
Pro Pro Cys Pro Ala Pro Glu Leu Leu Gly Gly Pro Ser Val Phe Leu
                325                 330                 335
Phe Pro Pro Lys Pro Lys Asp Thr Leu Met Ile Ser Arg Thr Pro Glu
                340                 345                 350
Val Thr Cys Val Val Val Asp Val Ser His Glu Asp Pro Glu Val Lys
                355                 360                 365
Phe Asn Trp Tyr Val Asp Gly Val Glu Val His Asn Ala Lys Thr Lys
                370                 375                 380
Pro Arg Glu Glu Gln Tyr Asn Ser Thr Tyr Arg Val Val Ser Val Leu
385                 390                 395                 400
Thr Val Leu His Gln Asp Trp Leu Asn Gly Lys Glu Tyr Lys Cys Lys
                405                 410                 415
Val Ser Asn Lys Ala Leu Pro Ala Pro Ile Glu Lys Thr Ile Ser Lys
                420                 425                 430
```

```
Ala Lys Gly Gln Pro Arg Glu Pro Gln Val Tyr Thr Leu Pro Pro Ser
        435                 440                 445

Arg Asp Glu Leu Thr Lys Asn Gln Val Ser Leu Thr Cys Leu Val Lys
    450                 455                 460

Gly Phe Tyr Pro Ser Asp Ile Ala Val Glu Trp Glu Ser Asn Gly Gln
465                 470                 475                 480

Pro Glu Asn Asn Tyr Lys Thr Thr Pro Pro Val Leu Asp Ser Asp Gly
                485                 490                 495

Ser Phe Phe Leu Tyr Ser Lys Leu Thr Val Asp Lys Ser Arg Trp Gln
            500                 505                 510

Gln Gly Asn Val Phe Ser Cys Ser Val Met His Glu Ala Leu His Asn
        515                 520                 525

His Tyr Thr Gln Lys Ser Leu Ser Leu Ser Pro Gly Gly Gly Gly Gly
    530                 535                 540

Ser Gly Gly Gly Gly Ser Gly Gly Gly Gly Ser Gly Gly Gly Gly Ser
545                 550                 555                 560

Gly Gly Gly Gly Ser Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
    610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
    690                 695                 700

Arg Asp Glu Leu Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly
785                 790                 795

<210> SEQ ID NO 7
<211> LENGTH: 802
<212> TYPE: PRT
<213> ORGANISM: Artificial Sequence
<220> FEATURE:
<223> OTHER INFORMATION: Synthesized

<400> SEQUENCE: 7
```

-continued

```
Asp Lys Glu Ala Leu Ser Glu Ala Gln Arg Thr Cys Pro Val Val Thr
 1               5                  10                 15
Cys Ala Leu Pro Gly Arg Asp Gly Arg Asp Gly Leu Lys Gly Glu Lys
                20                  25                 30
Gly Glu Pro Gly Gln Gly Leu Arg Gly Leu Gln Gly Pro Pro Gly Lys
                35                  40                 45
Val Gly Pro Pro Gly Asn Thr Gly Ala Pro Gly Ala Pro Gly Leu Lys
 50                  55                  60
Gly His Lys Gly Asp Arg Gly Asp Gly Gly Gly Ser Gly Gly Gly Gly
 65                  70                  75                 80
Gly Ser Gly Gly Gly Ser Arg Asn Asp Ala Gln Pro Ala Val Tyr
                85                  90                  95
Leu Phe Gln Pro Ser Pro Asp Gln Leu His Thr Gly Ser Ala Ser Val
               100                 105                 110
Val Cys Leu Leu Asn Ser Phe Tyr Pro Lys Asp Ile Asn Val Lys Trp
               115                 120                 125
Lys Val Asp Gly Val Ile Gln Asp Thr Gly Ile Gln Glu Ser Val Thr
               130                 135                 140
Glu Gln Asp Lys Asp Ser Thr Tyr Ser Leu Ser Ser Thr Leu Thr Met
145                 150                 155                 160
Ser Ser Thr Glu Tyr Leu Ser His Glu Leu Tyr Ser Cys Glu Ile Thr
               165                 170                 175
His Lys Ser Leu Pro Ser Thr Leu Ile Lys Ser Phe Gln Arg Ser Glu
               180                 185                 190
Cys Gln Arg Val Asp Gly Gly Gly Ser Gly Gly Gly Gly Ser Ala
               195                 200                 205
Ser Thr Thr Ala Pro Ser Val Phe Pro Leu Ala Pro Ser Cys Gly Ser
210                 215                 220
Thr Ser Gly Ser Thr Val Ala Leu Ala Cys Leu Val Ser Gly Tyr Phe
225                 230                 235                 240
Pro Glu Pro Val Thr Val Ser Trp Asn Ser Gly Ser Leu Thr Ser Gly
               245                 250                 255
Val His Thr Phe Pro Ser Val Leu Gln Ser Ser Gly Leu Tyr Ser Leu
               260                 265                 270
Ser Ser Met Val Thr Val Pro Ser Ser Arg Trp Pro Ser Glu Thr Phe
               275                 280                 285
Thr Cys Asn Val Ala His Pro Ala Ser Lys Thr Lys Val Asp Lys Pro
               290                 295                 300
Val Pro Lys Arg Glu Asn Gly Arg Val Pro Arg Pro Pro Asp Cys Pro
305                 310                 315                 320
Lys Cys Pro Ala Pro Glu Met Leu Gly Gly Pro Ser Val Phe Ile Phe
               325                 330                 335
Pro Pro Lys Pro Lys Asp Thr Leu Leu Ile Ala Arg Thr Pro Glu Val
               340                 345                 350
Thr Cys Val Val Val Asp Leu Asp Pro Glu Asp Pro Glu Val Gln Ile
               355                 360                 365
Ser Trp Phe Val Asp Gly Lys Gln Met Gln Thr Ala Lys Thr Gln Pro
               370                 375                 380
Arg Glu Glu Gln Phe Asn Gly Thr Tyr Arg Val Val Ser Val Leu Pro
385                 390                 395                 400
Ile Gly His Gln Asp Trp Leu Lys Gly Lys Gln Phe Thr Cys Lys Val
               405                 410                 415
```

```
Asn Asn Lys Ala Leu Pro Ser Pro Ile Glu Arg Thr Ile Ser Lys Ala
            420                 425                 430

Arg Gly Gln Ala His Gln Pro Ser Val Tyr Val Leu Pro Pro Ser Arg
        435                 440                 445

Glu Glu Leu Ser Lys Asn Thr Val Ser Leu Thr Cys Leu Ile Lys Asp
    450                 455                 460

Phe Phe Pro Asp Ile Asp Val Glu Trp Gln Ser Asn Gly Gln Gln
465                 470                 475                 480

Glu Pro Glu Ser Lys Tyr Arg Thr Thr Pro Pro Gln Leu Asp Glu Asp
                485                 490                 495

Gly Ser Tyr Phe Leu Tyr Ser Lys Leu Ser Val Asp Lys Ser Arg Trp
            500                 505                 510

Gln Arg Gly Asp Thr Phe Ile Cys Ala Val Met His Glu Ala Leu His
        515                 520                 525

Asn His Tyr Thr Gln Lys Ser Leu Ser His Ser Pro Gly Gly Gly Gly
    530                 535                 540

Gly Ser Gly Gly Gly Ser Gly Gly Gly Ser Gly Gly Gly Gly
545                 550                 555                 560

Ser Gly Gly Gly Ser Pro Lys Arg Glu Asn Gly Arg Val Pro Arg
                565                 570                 575

Pro Pro Asp Cys Pro Lys Cys Pro Ala Pro Glu Met Leu Gly Gly Pro
            580                 585                 590

Ser Val Phe Ile Phe Pro Pro Lys Pro Lys Asp Thr Leu Leu Ile Ala
        595                 600                 605

Arg Thr Pro Glu Val Thr Cys Val Val Val Asp Leu Asp Pro Glu Asp
    610                 615                 620

Pro Glu Val Gln Ile Ser Trp Phe Val Asp Gly Lys Gln Met Gln Thr
625                 630                 635                 640

Ala Lys Thr Gln Pro Arg Glu Glu Gln Phe Asn Gly Thr Tyr Arg Val
                645                 650                 655

Val Ser Val Leu Pro Ile Gly His Gln Asp Trp Leu Lys Gly Lys Gln
            660                 665                 670

Phe Thr Cys Lys Val Asn Asn Lys Ala Leu Pro Ser Pro Ile Glu Arg
        675                 680                 685

Thr Ile Ser Lys Ala Arg Gly Gln Ala His Gln Pro Ser Val Tyr Val
    690                 695                 700

Leu Pro Pro Ser Arg Glu Glu Leu Ser Lys Asn Thr Val Ser Leu Thr
705                 710                 715                 720

Cys Leu Ile Lys Asp Phe Phe Pro Pro Asp Ile Asp Val Glu Trp Gln
                725                 730                 735

Ser Asn Gly Gln Gln Glu Pro Glu Ser Lys Tyr Arg Thr Thr Pro Pro
            740                 745                 750

Gln Leu Asp Glu Asp Gly Ser Tyr Phe Leu Tyr Ser Lys Leu Ser Val
        755                 760                 765

Asp Lys Ser Arg Trp Gln Arg Gly Asp Thr Phe Ile Cys Ala Val Met
    770                 775                 780

His Glu Ala Leu His Asn His Tyr Thr Gln Lys Ser Leu Ser His Ser
785                 790                 795                 800

Pro Gly

<210> SEQ ID NO 8
<211> LENGTH: 779
<212> TYPE: PRT
<213> ORGANISM: Artificial Sequence
```

<220> FEATURE:
<223> OTHER INFORMATION: Synthesized

<400> SEQUENCE: 8

```
Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys Gln Arg Val Asp Gly Gly
            100                 105                 110

Gly Gly Ser Gly Gly Gly Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Asp Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Asn Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400
```

-continued

Thr Thr Pro Pro Gln Leu Asp Glu Asp Gly Ser Tyr Phe Leu Tyr Ser
            405                 410                 415

Lys Leu Ser Val Asp Lys Ser Arg Trp Gln Arg Gly Asp Thr Phe Ile
        420                 425                 430

Cys Ala Val Met His Glu Ala Leu His Asn His Tyr Thr Gln Lys Ser
            435                 440                 445

Leu Ser His Ser Pro Gly Gly Gly Gly Ser Gly Gly Gly Gly Ser
450                 455                 460

Gly Gly Gly Gly Ser Gly Gly Gly Ser Gly Gly Gly Ser Pro
465                 470                 475                 480

Lys Arg Glu Asn Gly Arg Val Pro Arg Pro Asp Cys Pro Lys Cys
            485                 490                 495

Pro Ala Pro Glu Met Leu Gly Gly Pro Ser Val Phe Ile Phe Pro Pro
            500                 505                 510

Lys Pro Lys Asp Thr Leu Leu Ile Ala Arg Thr Pro Glu Val Thr Cys
            515                 520                 525

Val Val Val Asp Leu Asp Pro Glu Asp Pro Glu Val Gln Ile Ser Trp
530                 535                 540

Phe Val Asp Gly Lys Gln Met Gln Thr Ala Lys Thr Gln Pro Arg Glu
545                 550                 555                 560

Glu Gln Phe Asn Gly Thr Tyr Arg Val Val Ser Val Leu Pro Ile Gly
                565                 570                 575

His Gln Asp Trp Leu Lys Gly Lys Gln Phe Thr Cys Lys Val Asn Asn
            580                 585                 590

Lys Ala Leu Pro Ser Pro Ile Glu Arg Thr Ile Ser Lys Ala Arg Gly
            595                 600                 605

Gln Ala His Gln Pro Ser Val Tyr Val Leu Pro Pro Ser Arg Glu Glu
610                 615                 620

Leu Ser Lys Asn Thr Val Ser Leu Thr Cys Leu Ile Lys Asp Phe Phe
625                 630                 635                 640

Pro Pro Asp Ile Asp Val Glu Trp Gln Ser Asn Gly Gln Gln Glu Pro
            645                 650                 655

Glu Ser Lys Tyr Arg Thr Thr Pro Pro Gln Leu Asp Glu Asp Gly Ser
            660                 665                 670

Tyr Phe Leu Tyr Ser Lys Leu Ser Val Asp Lys Ser Arg Trp Gln Arg
            675                 680                 685

Gly Asp Thr Phe Ile Cys Ala Val Met His Glu Ala Leu His Asn His
            690                 695                 700

Tyr Thr Gln Lys Ser Leu Ser His Ser Pro Gly Gly Gly Gly Ser
705                 710                 715                 720

Gly Pro Pro Gly Ile Ser Lys Glu Gly Pro Pro Gly Asp Pro Gly Leu
            725                 730                 735

Pro Gly Lys Asp Gly Asp His Gly Lys Pro Gly Ile Gln Gly Gln Pro
            740                 745                 750

Gly Pro Pro Gly Ile Cys Asp Pro Ser Leu Cys Phe Ser Val Ile Val
            755                 760                 765

Gly Arg Asp Pro Phe Arg Lys Gly Pro Asn Tyr
770                 775

<210> SEQ ID NO 9
<211> LENGTH: 5
<212> TYPE: PRT
<213> ORGANISM: Artificial Sequence
<220> FEATURE:

```
<223> OTHER INFORMATION: Synthesized

<400> SEQUENCE: 9

Gly Gly Gly Gly Ser
1               5

<210> SEQ ID NO 10
<211> LENGTH: 25
<212> TYPE: PRT
<213> ORGANISM: Artificial Sequence
<220> FEATURE:
<223> OTHER INFORMATION: Synthesized in La

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```